United States Patent
Giacalone et al.

(10) Patent No.: US 10,124,024 B2
(45) Date of Patent: Nov. 13, 2018

(54) IONIZING IRRADIATION STERILIZATION OF BACTERIAL MINICELL-BASED BIOPHARMACEUTICALS AND METHODS OF USE

(71) Applicant: Vaxiion Therapeutics, LLC, San Diego, CA (US)

(72) Inventors: Matthew J. Giacalone, San Diego, CA (US); Gary H. Ward, San Diego, CA (US)

(73) Assignee: Vaxiion Therapeutics, LLC, San Diego, CA (US)

( * ) Notice: Subject to any disclaimer, the term of this patent is extended or adjusted under 35 U.S.C. 154(b) by 0 days.

(21) Appl. No.: 15/887,432

(22) Filed: Feb. 2, 2018

(65) Prior Publication Data

US 2018/0153942 A1 Jun. 7, 2018

Related U.S. Application Data

(63) Continuation of application No. PCT/US2016/045400, filed on Aug. 3, 2016.

(60) Provisional application No. 62/200,903, filed on Aug. 4, 2015.

(51) Int. Cl.
| | |
|---|---|
| *A61K 35/74* | (2015.01) |
| *A61K 9/00* | (2006.01) |
| *A61K 47/26* | (2006.01) |
| *A61L 2/00* | (2006.01) |
| *C07K 14/24* | (2006.01) |
| *C07K 14/33* | (2006.01) |

(52) U.S. Cl.
CPC ............ *A61K 35/74* (2013.01); *A61K 9/0019* (2013.01); *A61K 47/26* (2013.01); *A61L 2/0035* (2013.01); *C07K 14/24* (2013.01); *C07K 14/33* (2013.01); *A61L 2202/21* (2013.01); *Y02A 50/475* (2018.01)

(58) Field of Classification Search
None
See application file for complete search history.

(56) References Cited

U.S. PATENT DOCUMENTS

| | | | |
|---|---|---|---|
| 4,895,724 | A | 1/1990 | Cardinal et al. |
| 5,314,695 | A | 5/1994 | Brown |
| 7,183,105 | B2 | 2/2007 | Sabbadini et al. |
| 7,611,885 | B2 | 11/2009 | Brahmbhatt et al. |
| 9,169,495 | B2 | 10/2015 | Brahmbhatt et al. |
| 2004/0265994 | A1 | 12/2004 | Brahmbhatt et al. |
| 2007/0298056 | A1 | 12/2007 | Brahmbhatt et al. |
| 2008/0051469 | A1 | 2/2008 | Brahmbhatt et al. |
| 2010/0112670 | A1 | 5/2010 | Giacalone et al. |

FOREIGN PATENT DOCUMENTS

| | | |
|---|---|---|
| WO | WO 98/52547 | 11/1998 |
| WO | WO 2012/112696 A1 | 8/2012 |
| WO | WO 2014/055682 A1 | 4/2014 |

OTHER PUBLICATIONS

Lowy, et al., Antiviral Res., 52:261. (Year: 2001).*
Kato et al., "Expression of the *lacZ* gene in *Escherichia coli* irradiated with gamma rays" Journal of Radiation Research and Applied Sciences, 2014, vol. 7, pp. 568-571.
International Search Report dated Sep. 27, 2016 in PCT/US2016/045400, filed Aug. 3, 2016.
Paterson, M. C. et al., "Endonucleolytic Activity from Micrococcus luteus That Acts on γ-Ray-Induced Damage in Plasmid DNA of *Escherichia coli* Minicells", Proc. Nat. Acad. Sci. USA, 1972, vol. 69, No. 10, pp. 2927-2931.
Michael J. Daly, "Death by protein damage in irradiated cells", DNA Repair 11 (2012) 12-21.
Verherstraeten, et al., "Perfringolysin O: The Underrated *Clostridium perfringens* Toxin?" Toxins 2015, 7, 1702-1721.

* cited by examiner

*Primary Examiner* — Michael Barker
(74) *Attorney, Agent, or Firm* — Knobbe Martens Olson & Bear LLP

(57) ABSTRACT

Disclosed herein are methods of terminally sterilizing bacterial minicells or compositions comprising bacterial minicells by exposure to ionizing irradiation. Also disclosed are terminally sterilized bacterial minicells, pharmaceutical compositions comprising the bacterial minicells, and methods of use the bacterial minicells and pharmaceutical compositions.

12 Claims, 15 Drawing Sheets

Before

After 25kGy

IONIZING IRRADIATION STERILIZATION OF BACTERIAL MINICELL-BASED BIOPHARMACEUTICALS AND METHODS OF USE

RELATED APPLICATIONS

The present application is a continuation of, and claims the benefit of priority to, PCT Application No. PCT/US2016/045400 filed Aug. 3, 2016, which claims priority under 35 U.S.C. § 119(e) to U.S. Provisional Application No. 62/200,903, filed on Aug. 4, 2015. The content of these related applications is herein expressly incorporated by reference in its entirety.

BACKGROUND

Field

The present application is drawn to compositions and methods for the production, purification, formulation, and terminal sterilization of eubacterial minicells for use as diagnostic, therapeutic, and prophylactic biopharmaceutical products and agents for the detection, treatment, and prevention of cancer, genetic disorders, infectious disease, and other maladies.

Description of the Related Art

The following description of the background of the invention is provided to aid in understanding the invention, but is not admitted to describe or constitute prior art to the invention. The contents of the articles, patents, and patent applications, and all other documents and electronically available information mentioned or cited in this application, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The use of bacterial minicells and other biocompatible microparticles and nanoparticles as small molecule drug and macromolecule drug delivery vehicles has been a growing area of interest in the development of new biopharmaceutical products designed to selectively target and treat cancer and/or act as vaccines. Bacterial minicells are spherical nano-sized (about 400 nm) particles that can be generated from recombinant minicell-producing bacterial strains. Minicells contain all of the components and molecular constituents of their parental bacteria with the exception of the bacterial chromosome. As a result, minicells are not living, cannot replicate, and are non-infectious, making them highly suitable as in vivo delivery vehicles and vaccines with no risk of infection. As described in more detail herein, because minicells are derived from bacterial strains that are highly amenable to recombinant engineering, recombinant expression techniques, and facile molecular biological techniques, they too are highly amenable to recombinant engineering and compared to other nanodelivery technologies, are easily converted into targeted drug delivery and vaccine vehicles.

One of the major impediments in the development of recombinant bacterial minicell-based biopharmaceuticals for use in humans has been the ability to reliably sterilize these products using conventional standardized filter-based methodologies as minicells oftentimes remain in the retenate and do not readily pass through a standard 0.22 micron filter membrane. Other filtration-based methodologies used to purify minicells as biopharmaceutical products, as described in US 2004/0265994, provide no assurance of consistent sterility using a validated sterilization method in view of ICH guidelines. In addition, this method introduces multiple additional steps to the downstream processing of minicells including long incubations in the presence of antibiotics and high salt concentrations, each of which would require additional characterization testing for their respective removal in final drug product.

Accordingly, there is a need for effective and reliable methods for sterilizing bacterial minicell-based biopharmaceutical products.

SUMMARY

Disclosed herein is a method of producing terminally sterilizing bacterial minicells intended for pharmaceutical use, comprising exposing a composition comprising a plurality of bacterial minicells to ionizing irradiation. The ionizing irradiation can be, for example, gamma irradiation, E-beam (electron beam, beta irradiation) irradiation, X-ray (photon) irradiation, and UV irradiation. One of the preferred types of ionizing irradiation is gamma irradiation. In some embodiments, the ionizing irradiation is at a dose of about 5 kGy to about 40 kGy. In some embodiments, the ionizing irradiation is at a dose of about 25 kGy. In some embodiments, the dose of the gamma irradiation is sufficient to sterilize the composition to a level conforming to USP <71> standards under version USP 38 NF 33.

In some embodiments, the composition is a pharmaceutical composition comprising said bacterial minicells and a pharmaceutically acceptable excipient. In some embodiments, the method comprises producing a pharmaceutical composition comprising said bacterial minicells and a pharmaceutically acceptable excipient. In some embodiments, pharmaceutically acceptable excipient is trehalose. In some embodiments, the composition is a pharmaceutical composition comprising said bacterial minicells and a pharmaceutically acceptable diluent. In some embodiments, the method comprises producing a pharmaceutical composition comprising said bacterial minicells and a pharmaceutically acceptable diluent. In some embodiments, the pharmaceutically acceptable diluent is sterile water.

In some embodiments, the bacterial minicells are exposed to a terminally sterilizing dose of ionizing irradiation as a frozen suspension. In some embodiments, the composition is exposed to a terminally sterilizing dose of ionizing irradiation as a frozen suspension. In some embodiments, the bacterial minicells are exposed to a terminally sterilizing dose of ionizing irradiation as a frozen lyophile. In some embodiments, the composition is exposed to a terminally sterilizing dose of ionizing irradiation as a frozen lyophile.

In some embodiments, the bacterial minicells express and/or display invasin or a functional equivalent thereof. The invasin can be, for example, an invasin from *Yersinia pseudotuberculosis*. In some embodiments, the bacterial minicells comprise perfringolysin O (PFO).

Also disclosed herein is a pharmaceutical composition comprising a plurality of bacterial minicells, wherein said bacterial minicells have been exposed to ionizing irradiation. In some embodiments, the pharmaceutical composition is sterile. In some embodiments, the bacterial minicells or the pharmaceutical composition has been terminally sterilized. In some embodiments, the pharmaceutical composition has been exposed to ionizing irradiation.

In some embodiments, the bacterial minicells comprise targeted therapeutic minicells. In some embodiments, the bacterial minicells comprise immunodulatory minicells. In some embodiments, the bacterial minicells comprise immunogenic minicells. In some embodiments, the bacterial minicells are derived from a bacterium from the genus *Escherichia* spp., *Salmonella* spp., *Listeria* spp., *Pseudomonas* spp., *Acinetobacter* spp., *Neiserria* spp., *Shigella* spp., *Bacillus* spp., or *Haemophilus* spp.

In some embodiments, the pharmaceutical composition further comprises a pharmaceutically acceptable excipient. The pharmaceutically acceptable excipient can be, for example, trehalose. In some embodiments, the pharmaceutical composition further comprises a pharmaceutically acceptable diluent. The pharmaceutically acceptable diluent can be, for example, sterile water.

In some embodiments, viable microbial contaminants in the pharmaceutical composition are at a level conforming to USP <71> standards under version USP 38 NF 33.

In some embodiments, the bacterial minicells express and/or display invasin or a functional equivalent thereof. For example, the invasin can be an invasin from *Yersinia pseudotuberculosis*. In some embodiments, the bacterial minicells comprise perfringolysin O (PFO).

In some embodiments, the pharmaceutical composition is in the form of a frozen suspension. In some embodiments, the pharmaceutically composition is in the form of a frozen lyophile.

Also provided herein is a biopharmaceutical composition which comprises a plurality of bacterial minicells that have been exposed to a sterilizing dose of ionizing gamma irradiation. In some embodiments, the biopharmaceutical composition is sterile within the meaning of US Pharmacopeia <71>, and wherein the bacterial cells (1) express and/or display invasin on the minicell surface, and (ii) comprise perfringolysin O as a bioactive payload, the activity of which is not affected by exposure to a sterilizing dose of gamma irradiation

DETAILED DESCRIPTION

Figure 1:
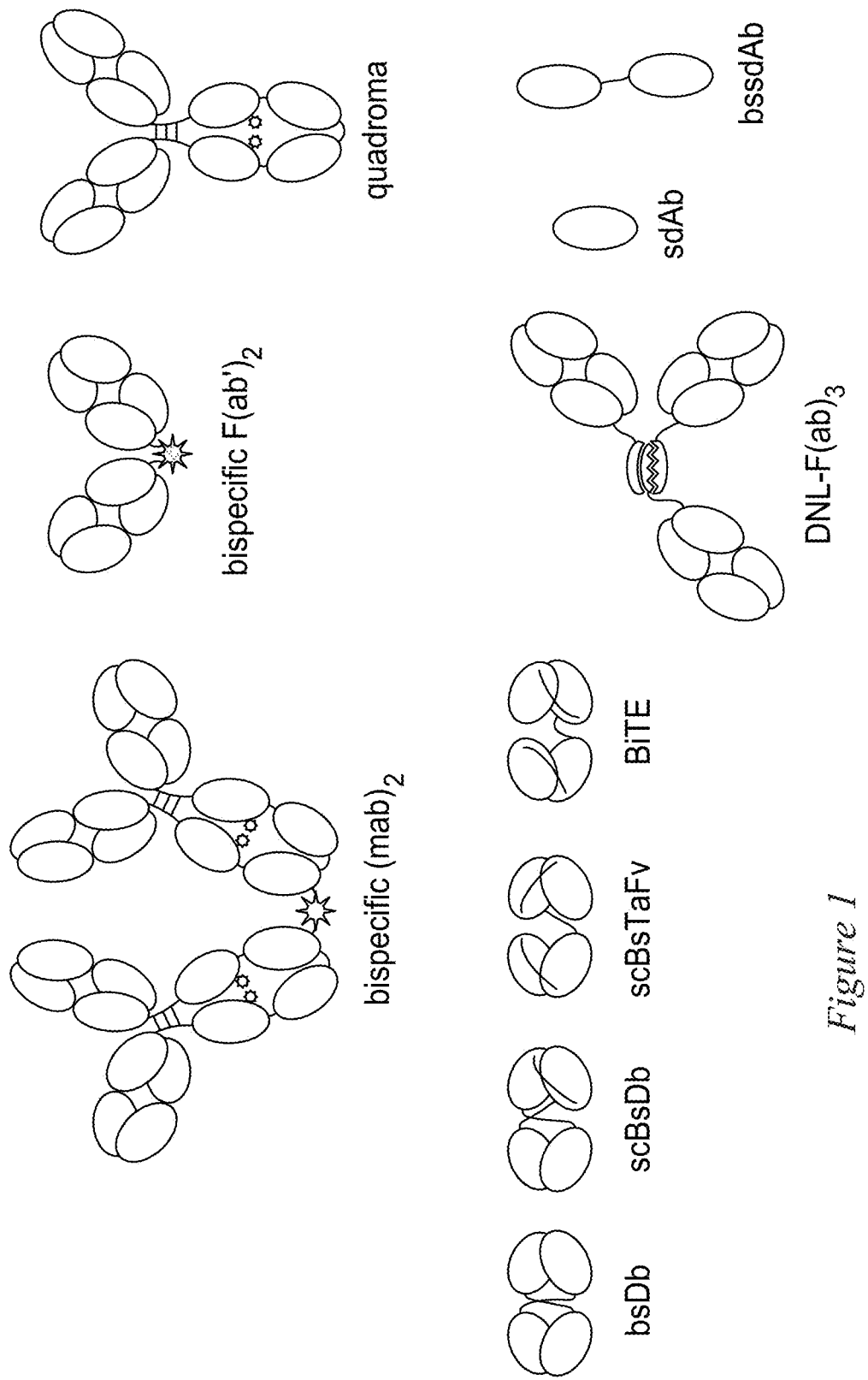
FIG. 1 is a schematic illustration of non-limiting exemplary types of bi-specific antibodies and bi-specific antibody derivatives that are suitable for use in the embodiments described herein.

In the following detailed description, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, can be arranged, substituted, combined, and designed in a wide variety of different configurations, all of which are explicitly contemplated and make part of this disclosure.

Unless defined otherwise, all technical and scientific terms used herein have the same meaning as commonly understood by one of ordinary skill in the art. Although the present application has been described with reference to embodiments and examples, it should be understood that various modifications can be made without departing from the spirit of the invention. All references cited herein are expressly incorporated herein by reference in their entirety.

Embodiments of the present application are disclosed in further detail in the following examples, which are not in any way intended to limit the scope of the present application.

Definitions

As used herein, the term "immunomodulatory minicells" refers to minicells that are capable of activating, de-activating, or influencing the immune system in such a way as to be beneficial or therapeutic to a mammalian recipient suffering from disease.

As used herein, the term "immunogenic minicells" refers to minicells that are capable of stimulating an adaptive immune response against a particular antigen, antigens, pathogenic organism, opportunistic organism, parasitic organism, or cancer cells (i.e. a vaccine).

As used herein, the term "immunotherapy" refers to the use of an immunomodulatory compound, preferably an immunomodulatory minicell, to generate, enhance, impede, or otherwise influence an immune response, the result of which has a beneficial effect with respect to the elimination or slowing the progression of disease, especially cancer.

As used herein, the term "adherent minicell" refers to a minicell that is capable of binding and adhering to the surface of a non-constitutively phagocytic eukaryotic cell without stimulating appreciable endocytosis of said minicells.

As used herein, the term "muco-adherent minicell" refers to a minicell that is capable of binding and adhering to a mucosal surface.

As used herein, the term "targeted minicells" refers to minicells that have been modified, for example via recombinant engineering and/or the addition of exogenous targeting moieties (e.g. antibodies and antibody derivatives), to selectively target specific tissues, organs, and/or cells.

As used herein, the term "targeted therapeutic minicells" refers to minicells that have been modified, for example, either via recombinant engineering and/or the addition of exogenous targeting moieties (e.g. antibodies and antibody derivatives), to selectively target specific tissues, organs, and/or cells and further contain small molecule drugs, therapeutic nucleic acids, therapeutic polypeptides, and any combination of the preceding.

As used herein, the term "targeted minicell vaccine" refers to bacterial minicells that encapsulate a protein antigen and/or a nucleic acid-based vaccine (e.g. DNA or RNA-based vaccine) derived from an infectious disease agent or from a tumor cell of choice, wherein the minicell further expresses and/or displays targeting moieties conferring specificity for antigen presenting cells of the immune system on the surface (e.g., external surface) of said minicells in such a way that they are able to specifically bind to, are bound by, or in some other way specifically recognize and thereby deliver, localize to, or aggregate within antigen presenting cells, organs, or tissue types involved in the genesis, progression, and/or maintenance of a recipient host immune response, to deliver the antigenic contents of the minicell to the antigen presenting target cell, tissue, and organ type in vitro or in vivo. Such a targeted minicell vaccine may also comprise recombinant chemokines, cytokines, or interleukin proteins and functional nucleic acids encoding for the same.

As used herein, the term "homotypic minicell vaccine" refers to bacterial minicells produced by a pathogenic bacterium, such that the minicell vaccine is protective against said pathogenic bacterium. A homotypic minicell vaccine may further comprise a protein antigen and/or a nucleic acid-based vaccine (e.g. DNA or RNA-based vaccine) derived from the same infectious disease agent. Such a homotypic minicell vaccine may also comprise recombinant chemokines, cytokines, or interleukin proteins and functional nucleic acids encoding for the same. Such a homotypic minicell vaccine may also be a targeted minicell vaccine.

As used herein, the term "Integrin-targeted minicells" refers to minicells that express and/or display invasin (for example, the pan-Beta1-integrin-targeting cell surface molecule Invasin from *Yersinia pseudotuberculosis*) and any functional equivalents thereof.

As used herein, the term "Integrin-targeted therapeutic minicells" refers to minicells that express and/or display invasin (for example, the pan-Beta1-integrin-targeting cell surface molecule Invasin from *Yersinia pseudotuberculosis*) and any functional equivalents thereof, wherein the minicells further comprise one or more bioactive molecules including but not limited to therapeutic polypeptides, small molecule drugs, therapeutic nucleic acids, and any combination of the preceding.

As used herein, the term "Integrin-targeted immunomodulatory minicells" refers to minicells that express and/or display invasin (for example, the pan-Beta1-integrin-targeting cell surface molecule Invasin from *Yersinia pseudotuberculosis*) and any functional equivalents thereof, wherein the minicells further comprise one or more bioactive molecules including but not limited to immunomodulatory polypeptides, small molecule drugs, immunomodulatory nucleic acids, and any combination of the preceding.

As used herein, the term "VAX-IP minicells" refers to minicells that express and/or display invasin (for example, the pan-Beta1-integrin-targeting cell surface molecule Invasin from *Yersinia pseudotuberculosis*) and any functional equivalents thereof, wherein the minicells further comprise perfringolysin O (PFO).

As used herein, the term "VAX014 minicells" refers to VAX-IP minicells that have been formulated in a pharmaceutical composition which comprises sterile D-trehalose as an excipient.

As used herein, the term "VAX-IPT minicells" refers to minicells that express and/or display invasin (for example, the pan-Beta1-integrin-targeting cell surface molecule Invasin from *Yersinia pseudotuberculosis*) and any functional equivalents thereof, wherein the minicells further comprise perfringolysin O (PFO) and a protein toxin.

As used herein, the term "VAX-IPP minicells" refers to minicells that express and/or display invasin (for example, the pan-Beta1-integrin-targeting cell surface molecule Invasin from *Yersinia pseudotuberculosis*) and any functional equivalents thereof, wherein the minicells comprise perfringolysin O (PFO) and an exogenous polypeptide other than a protein toxin.

As used herein, the term "VAX-IPD minicells" refers to minicells that express and/or display invasin (for example, the pan-Beta1-integrin-targeting cell surface molecule Invasin from *Yersinia pseudotuberculosis*) and any functional equivalents thereof, wherein the minicells comprise perfringolysin O (PFO) and a catalytic fragment of diphtheria toxin.

As used herein, the term "prokaryotic cell division gene" refers to a gene that encodes a gene product that participates in the prokaryotic cell division process. Many cell division genes have been discovered and characterized in the art. Examples of cell division genes include, but are not limited to, zipA, sulA, secA, dicA, dicB, dicC, dicF, ftsA, ftsI, ftsN, ftsK, ftsL, ftsQ, ftsW, ftsZ, minC, minD, minE, seqA, ccdB, sfiC, and ddlB.

As used herein, the term "transgene" refers to a gene or genetic material that has been transferred naturally or by any genetic engineering techniques from one organism to another. In some embodiments, the transgene is a segment of DNA containing a gene sequence that has been isolated from one organism and is introduced into a different organism. This non-native segment of DNA may retain the ability to produce RNA and/or protein in the transgenic organism, or it may alter the normal function of the transgenic organism's genetic code. In some embodiments, the transgene is an artificially constructed DNA sequence, regardless of whether it contains a gene coding sequence, which is introduced into an organism in which the transgene was previously not found.

As used herein, an agent is said to have been "purified" if its concentration is increased, and/or the concentration of one or more undesirable contaminants is decreased, in a composition relative to the composition from which the agent has been purified. In some embodiments, purification includes enrichment of an agent in a composition and/or isolation of an agent therefrom.

The term "sufficiently devoid of viable parental cells", synonymous with "sufficiently devoid", as used herein refers to a composition of purified minicells that have a viable parental cell contamination level that has little or no effect on the toxicity profile and/or therapeutic effect of targeted therapeutic minicells.

The term "sterilized" as used herein means to be sufficiently devoid of bioburden as to satisfy the requirements under the standard Sterility Testing <71> of the United States Pharmacopeia version USP 38 NF 33, its harmonized foreign counter parts, and other approved international pharmaceutical standards.

The term "terminally sterilized" as used herein refers to the final step in a drug manufacturing process wherein the final drug product is found to be sufficiently devoid of bioburden as to satisfy the requirements under the standard Sterility Testing <71> of the United States Pharmacopeia version USP 38 NF 33, its harmonized foreign counter parts, and other approved international pharmaceutical standards. A terminally sterilized drug product can be ready for administration to a subject.

The term "domain" or "protein domain" used herein refers to a region of a molecule or structure that shares common physical and/or chemical features. Non-limiting examples of protein domains include hydrophobic transmembrane or peripheral membrane binding regions, globular enzymatic or receptor regions, protein-protein interaction domains, and/or nucleic acid binding domains.

The terms "eubacteria" and "prokaryote" are used herein as these terms are used by those in the art. The term "prokaryotic" used herein encompasses, for example, Eubacteria, including both Gram-negative and Gram-positive bacteria, prokaryotic viruses (e.g., bacteriophage), and obligate intracellular parasites (e.g., Richettsia, Chlamydia, etc.).

The term "immunomodulatory polypeptide" used herein refers to any collection of diverse protein molecule types that have an immunomodulatory effect when introduced into a eukaryotic organism or cell (e.g., a mammal such as human). An immunomodulatory polypeptide can be a cytokine, a chemokine, a cholesterol-dependent cytolysin, a functional enzyme, an antibody or antibody mimetic, an activated caspase, a pro-caspase, a cytokine, a chemokine, a cell-penetrating peptide, or any combination and/or plurality of the proceeding. The term should not be confused with the word "immunogen" or "antigen", each of which is described below.

The terms "immunogen" and "antigen" are interchangeable and used herein to refer to polypeptides, carbohydrates, lipids, nucleic acids, and other molecules to which an antigen-specific antibody, cellular, and/or allergenic response may be mounted against. Antigen-specific immune responses shall rely on the presence of the antigen/immunogen, and shall not be included in the definition of immunomodulatory responses as used herein.

The term "overexpression" used herein refers to the expression of a functional nucleic acid, polypeptide or protein encoded by DNA in a host cell, wherein the nucleic acid, polypeptide or protein is either not normally present in the host cell, or wherein the nucleic acid, polypeptide or protein is present in the host cell at a higher level than that normally expressed from the endogenous gene encoding the nucleic acid, polypeptide or protein.

The term "modulate" as used herein means to interact with a target either directly or indirectly so as to alter the activity of the target to regulate a biological process. The mode of "modulate" includes, but is not limited to, enhancing the activity of the target, inhibiting the activity of the target, limiting the activity of the target, extending the activity of the target, and attenuating the activity of the target.

The term "heterologous" as used herein refers to a protein, gene, nucleic acid, imaging agent, buffer component, or any other biologically active material that is not naturally found in a minicell or minicell-producing bacterial strain (for example, has been recombinantly introduced or transformed into the minicell-producing parent cell) that is expressed, transcribed, translated, amplified or otherwise generated by minicell-producing bacterial strains that harbor recombinant genetic material coding for said heterologous material or coding for genes that are capable of producing said heterologous material (e.g., a bioactive metabolite not native to the parent cell).

The term "exogenous" as used herein refers to a protein (e.g., antibodies), gene(s), nucleic acid(s), small molecule drug(s), imaging agent(s), buffer, radionuclide(s), or any other biologically active or inactive material that is not native to a cell, or in the case of a minicell, not native to the parent cell of the minicell (for example, has been recombinantly introduced or transformed into the minicell-producing parent cell). Exogenous material differs from heterologous material by virtue of the fact that it is generated, purified, and added separately.

The term "therapeutic" as used herein means having a biological effect or combination of biological effects that inhibits, eliminates, reduces, or prevents progression of a disease or other aberrant biological processes in an animal (including humans).

The term "prophylactic" as used herein means having a biological effect or combination of biological effects that prevents or delays progression or establishment of a disease, disease state, or other aberrant biological processes in an animal (including humans).

The term "diagnostic" as used herein means having the ability to detect, monitor, follow, and/or identify a disease or condition in an animal (including humans) or from a biological sample including but not limited to blood, urine, saliva, sweat and fecal matters.

The term "theranostic" as used herein means having the combined effects of a therapeutic and a diagnostic composition.

The term "recombinantly expressed" as used herein means the expression of one or more nucleic acid(s) and/or protein(s) from a nucleic acid molecule that is artificially constructed using modern genetic engineering techniques wherein the artificially constructed nucleic acid molecule does not occur naturally in minicells and/or minicell-producing bacterial strains wherein the artificial nucleic acid molecule is present as an episomal nucleic acid molecule or as part of the minicell-producing bacterial chromosome.

The term "episomal" as used herein refers to a nucleic acid molecule that is independent of the chromosome(s) of a given organism or cell.

The term "detoxified" as used herein refers to a modification made to a composition or component thereof that results in a significant reduction in acute toxicity to the modified composition or component thereof, regardless of what the causative biological basis for toxicity to the composition or component thereof happens to be.

As used herein, the term "bioactive molecule" refers to a molecule having a biological effect on an eukaryotic organism or cell (e.g., a mammal such as human) when introduced into the eukaryotic organism or cell. Examples of bioactive molecules include, but are not limited to, therapeutic nucleic acids, therapeutic polypeptides (including protein toxins), and therapeutic small molecule drugs.

The present disclosure relates to the generation and use of terminally sterilized bacterial minicell-based compositions in vitro and in vivo for the targeted delivery of small molecule drugs, nucleic acids, polypeptides, and imaging agents to different tissues, organs, and cell types with intended use as medicaments in the treatment and prevention of cancer, infectious disease, autoimmune disease, genetic disorders, and other biological maladies in higher order animals including but not limited to those found in the phylum Chordata.

The present disclosure provides compositions and methods for the production of bacterial minicell-based pharmaceutical, diagnostic, and vaccine products where ionizing irradiation, for example high-dose ionizing irradiation, is employed to sterilize the product. In the context of generating sterile bacterial minicell-based biopharmaceuticals, the methods disclosed herein remove viable contaminating parental cells and other adventitious microbes while ensuring sterility, using fewer steps and eliminating the need for the addition of additional antibiotics or hypertonic conditions, while preserving minicell integrity, stability, and product function.

Bacterial minicells are achromosomal, membrane-encapsulated biological nanoparticles (approximately 250-500 nm in diameter) that are formed by bacteria following a disruption in the normal division apparatus of bacterial cells. In essence, minicells are small, metabolically active replicas of normal bacterial cells with the exception of chromosomal DNA and as such, are non-dividing, non-viable, and non-infectious. Bacterial minicells may be generated from a wide variety of Gram-negative and Gram-positive species and strains of bacteria including but not limited to *Escherichia* spp, *Salmonella* spp., *Pseudomonas* spp., *Listeria* spp., *Burkholderia*, spp., *Shigella* spp., *Bacillus* spp., *Acinetobacter* spp., *Franciscella* spp. *Legionella* spp., *Lactobacillus* spp., *Clostridium* spp., *Campylobacter* spp., *Neisseria* spp., *Chlamydia* spp., and the like. Although minicells do not contain bacterial chromosomes, plasmid DNA molecules (smaller than chromosomes), RNA molecules (of all subtypes and structures), native and/or recombinantly expressed proteins, nucleic acids, and other metabolites have all been shown to segregate into minicells. Minicells are uniquely suited as in vivo targeted drug delivery agents because they can be engineered to express and/or display surface-localized cell-specific targeting ligands such as antibodies or bacterial adhesins and invasins in combination with one or more different naturally occurring, heterologous, or exogenous therapeutic molecular components in a single particle. In short, minicells can be "engineered" to preferentially encapsulate, be coupled to, or absorb biologically active molecules, including but not limited to nucleic acids, proteins, small molecule drugs, and any combination thereof for subsequent delivery and generation of responses in both prophylactic and therapeutic medicinal applications where the prevention, maintenance, and/or inhibition of disease is desirable.

Genetically engineered bacterial minicells have been used directly as anticancer agents as described in U.S. Pat. No. 7,183,105, which is incorporated herein by reference in its entirety. For example, U.S. Pat. No. 7,183,105 describes that minicells can be engineered to use minicell surface-localized antibodies to target and deliver small molecule drugs, peptides, proteins, and various nucleic acids, together or in concert directly to cancer cells to exert a direct targeted anticancer effect. Other investigators have also reported the same findings as those taught in U.S. Pat. No. 7,183,105, with respect to the use of minicells as targeted delivery vehicles, as illustrated in US Patent Publication Nos. 20070298056 and 20080051469, and U.S. Pat. No. 9,169,495, each of which is incorporated herein by way of reference. Earlier work has described the use of bacterial minicells as potential vaccines and vaccine carriers, first as heterologous polypeptide antigen carriers, and later as nucleic acid-based vaccine carriers. More recent work has further expanded the repertoire of bacterial minicell-based therapies to include immunomodulatory compositions and methods.

Regardless of the final bacterial minicell-based product type, if intended for parenteral or topical medicinal or diagnostic use, reliable elimination of viable contaminating parental cells and any other adventitious microbes from the final active pharmaceutical ingredient (API) or final drug product (DP) is of paramount importance to reliable product safety and release for use. Many approaches have been used in the past to attempt to purify bacterial minicells from the viable parental cells that produce them. The most common approach used by researchers to purify bacterial minicells is a combination of differential centrifugation and one or more rounds of further purification using either linear or step density gradients. Other approaches have included but are not limited to filtration-based schemes, induction of lytic phage, and selective treatment with antibiotic(s) in combination with osmotic shock and/or sonication. Typical purity levels using these methods range from 1 viable contaminating parental cell in $10^5$-$10^8$ minicells. In recent years, newer methodologies have been described. For example, U.S. Pat. No. 7,611,885 described a method combining (i) differential centrifugation, (ii) two rounds of density gradient purification, (iii) cross-flow filtration through a 0.45 uM filter, (iv) treatment with a high concentration of salt to induce osmotic shock resulting in parent cell filamentation, (v) treatment with an antibiotic (vi) cross-flow filtration through a 0.2 uM filter, (vii) cross-flow filtration through a second 0.45 uM, (viii) concentration of minicells through a 100 kDa filter, (ix) treatment with anti-endotoxin antibodies couple to magnetic beads, (x) magnetic separation of endotoxin bound to said beads, (xi) collection of minicells, and then presumably (xii) formulation into excipient or other vehicle for final API generation. While the method described in U.S. Pat. No. 7,611,885 prophetically aspires to achieve a reduction in viable contaminating parental cells to levels as low as 1 in $10^{11}$ minicells, the method also results in considerable loss of minicells, addition of exogenous antibiotics and/or salts, and multiple filtration steps wherein adventitious microbes may be introduced during processing. Most importantly, the final filtration step relies on dead end filtration (i.e. retention of minicells) and is therefore not considered a terminally sterilizing event by FDA, other regulatory agencies operating under ICH guidelines, and other approved international pharmaceutical standards.

The present disclosure impinges on the unexpected finding that bacterial minicells can be terminally sterilized by exposure to ionizing irradiation, for example high dose ionizing irradiation, with no loss of potency, targeting ability, or stability while achieving the benefit of complete elimination of contaminating viable parental cells. This finding allows for the use of more scalable, conventional, GMP-compatible/compliant minicell purification methodologies while allowing a mechanism by which to terminally sterilize bacterial minicell-based biopharmaceutical products to a level sufficient to satisfy Sterility Testing standards under USP <71> version USP 38 NF 33 and its harmonized foreign equivalents.

It is well known that ionizing irradiation is capable of achieving sterility, as it is the sterilization methodology of choice for medical device and surgical instrument products. In the context of sterilization, ionizing irradiation works by generating free oxygen radicals. Free oxygen radicals are a highly reactive molecular species that quickly introduce breaks in the covalent bonds of nucleic acids and proteins, leading to cell and/or microbe death. In sterility applications it is commonly held that a dose of 5 kGy is sufficient to terminally sterilize, although more often than not a higher dose of 25 kGy is used to ensure sterility and complete absence of viable microbial growth. Because sterilization by ionizing irradiation at these dose levels is a potent, non-selective methodology for killing microbes, logic would follow that it would also have a detrimental effect on the stability and activity of bacterial minicells. The fact that exposure to sterilizing doses of ionizing irradiation has no effect on bacterial minicells yet renders all contaminating parental cells unviable is quite unexpected. Without being bound by any particular theory, one possibility is thought to be that ionizing irradiation only affects nucleic acids and not protein components, and because bacterial cells have a chromosome and minicells do not, that they are being selectively eliminated on that basis. However, if proteins were unaffected, bacterial cells exposed to ionizing irradiation at any level would be capable of utilizing these protein-based DNA repair systems to recover. Bacteria do not recover from exposure to ionizing irradiation levels beyond ~3 kGy, strongly supporting the notion that proteins are also affected at these doses. Other investigators have described a decrease in function of proteins in bacteria to levels as low as 10% when exposed to 6-8 kGy of gamma irradiation, further supporting the notion that protein function in bacteria is negatively affected by gamma irradiation (see Kato et al., Journal of Radiation Research and Applied Sciences, 2014, Volume 7, pp. 568-71). Furthermore, isolated proteins or protein mixtures that are exposed to ionizing irradiation are also quickly rendered inactive. The methods described in the present disclosure goes against what is known about the effects of ionizing irradiation on biomaterials and bacteria containing functional proteins, and as demonstrated herein that bacterial minicells and bacterial minicell-based biopharmaceutical products can be terminally sterilized by exposure to ionizing irradiation with no loss of integrity, specificity, stability, potency, and in vivo activity while eliminating all viable contaminating parental cells and/or adventitious microbes.

To further maximize safety and limit toxicity due to viability of any contaminating parental cells or the presence of lipopolysaccharide (endotoxin), in some embodiments, the minicells disclosed herein are derived from minicell-producing strains that comprise one or more of the three safety features disclosed below. In some embodiments, the minicell-producing strains comprise one or more of these three synergistic safety features. For example, the minicell-producing strain can comprise one, two, or all of these three safety features. The first is a genetic suicide mechanism that kills residual live parental cells without lysing them (and expelling free lipopolysaccharide) after the minicell formation step has been completed. The present application incorporates the use of a regulated genetic suicide mechanism that upon exposure to the appropriate inducer, introduces irreparable damage to the chromosomes of minicell-producing parental cells as described in US2010-0112670, incorporated by reference herein. The suicide mechanism operates to introduce irreparable double-stranded breaks to the chromosome of the parental cells and can be used as an adjunct to conventional separation techniques to improve minicell purification. The second safety feature is a defined auxotrophy, preferably but not necessarily in the diaminopimelic acid (DAP) biosynthesis pathway, and most preferably in the dapA gene of an E. coli minicell-producing strain. Minicell-producing strains of E. coli that exhibit DAP auxotrophy (dapA−) cannot survive outside of the laboratory without supplementation of DAP. Further, DAP is not found in mammals, including humans, and as such any minicell-producing parental cell that is present in the minicell product will not be able to survive in the environment outside of the laboratory or production facility or in vivo. Many variations on this theme exist for different Gram-negative and Gram-positive bacteria. For example, in Salmonella, spp., auxotrophies in the aromatic amino acid biosynthesis pathways (the aro genes) produce in effect, the same result. In the case of Shigella spp. auxotrophies in the guanine biosynthesis pathway will produce, in effect, the same result. The third safety feature entails a deletion of the lpxM gene in E. coli minicell-producing strains. Deletion of the lpxM gene can result in the production of de-toxified lipopolysaccharide (LPS) molecules. The lpxM gene (also referred to as the msbB gene) functions to add a terminal myristolic acid group to the lipid A portion of the LPS molecule and removal of this group (by way of elimination of the lpxM gene) results in marked detoxification of LPS. Specifically, detoxification is characterized by a decrease in the production of pro-inflammatory cytokines in response to exposure to LPS. It should be noted that this modification does not teach away from the present invention with respect to immunomodulatory minicell compositions as cytokine production in response to the detoxified form of LPS can still occur, albeit not at the same level as wildtype LPS. The detoxification controls only the levels of cytokines produced, making it possible to dampen the acute sepsis-like pro-inflammatory response while allowing more robust Th1 and/or Th2 immune responses, to be achieved without overt toxicity. This deletion can be introduced into any functionally equivalent gene of any Gram-negative or Gram-positive minicell-producing strain to achieve the same effect. The enhanced safety profile can reduce the risk of and potential for developing sepsis. From a regulatory and manufacturing perspective, it is also preferred that antibiotic resistance markers be eliminated from the bacterial chromosome of the minicell-producing parental cell strain. One or more of the safety features can be optional.

Some embodiments disclosed herein provide a method of making immunomodulatory minicells, comprising culturing the immunomodulatory minicell-producing bacteria disclosed herein and substantially separating immunomodulatory minicells from the minicell-producing parent cells, thereby generating a composition comprising immunotherapeutic minicells. In some embodiments, the method further comprises inducing immunomodulatory minicell formation from a culture of minicell-producing parent cells. In some embodiments, the method further comprises inducing expression of the gene encoding the genetic suicide endonuclease. In some embodiments, minicell formation is induced by the presence of one or more chemical compounds selected from isopropyl β-D-1-thiogalactopyranoside (IPTG), rhamnose, arabinose, xylose, fructose, melibiose, and tetracycline. In some embodiments, the expression of the gene encoding the genetic suicide endonuclease is induced by a change in temperature. In some embodiments, the method further comprises purifying the immunomodulatory minicells from the composition. In some embodiments, the immunomodulatory minicells are substantially separated from the parent cells by a process selected from the group including but not limited to centrifugation, filtration, ultrafiltration, ultracentrifugation, density gradient(s), immunoaffinity, immunoprecipitation, and any combination of the preceding purification methods. In some embodiments, immunomodulatory minicells are lyophilized. In some embodiments, immunomodulatory minicells are frozen. In some embodiments, immunomodulatory minicells are lyophilized and then frozen. In some embodiments, immunomodulatory minicells are formulated as a frozen suspension in a cryoprotectant excipient or other pharmaceutically acceptable carrier or GRAS substance. In some embodiments, immunomodulatory minicells are exposed to ionizing irradiation. In some embodiments, immunomodulatory minicells are terminally sterilized by exposure to ionizing irradiation. In some embodiments, immunomodulatory minicells are terminally sterilized by exposure to ionizing gamma irradiation.

Some embodiments provide a method of making immunogenic minicells for example, vaccines), comprising culturing the appropriate immunogenic minicell-producing bacteria disclosed herein and substantially separating immunogenic minicells from the minicell-producing parent cells, thereby generating a composition comprising immunogenic minicells. In some embodiments, the method further comprises inducing immunogenic minicell formation from a culture of minicell-producing parent cells. In some embodiments, the method further comprises inducing expression of the gene encoding the genetic suicide endonuclease. In some embodiments, minicell formation is induced by the presence of one or more chemical compounds selected from isopropyl β-D-1-thiogalactopyranoside (IPTG), rhamnose, arabinose, xylose, fructose, melibiose, and tetracycline. In some embodiments, the expression of the gene encoding the genetic suicide endonuclease is induced by a change in temperature. In some embodiments, the method further comprises purifying the immunogenic minicells from the composition. In some embodiments, the immunogenic minicells are substantially separated from the parent cells by a process selected from the group including but not limited to centrifugation, filtration, ultrafiltration, ultracentrifugation, density gradient(s), immunoaffinity, immunoprecipitation, and any combination of the preceding purification methods. In some embodiments, immunogenic minicells are lyophilized. In some embodiments, immunogenic minicells are frozen. In some embodiments, immunogenic minicells are lyophilized and then frozen. In some embodiments, immunogenic minicells are formulated as a frozen suspension in a cryoprotectant excipient or other pharmaceutically acceptable carrier or GRAS substance. In some embodiments, immunogenic minicells are exposed to ionizing irradiation. In some embodiments, immunogenic minicells are terminally sterilized by exposure to ionizing irradiation. In some embodiments, immunogenic minicells are terminally sterilized by exposure to ionizing gamma irradiation.

Some embodiments provide a method of making targeted therapeutic minicells, comprising culturing the targeted therapeutic minicell-producing bacteria disclosed herein and substantially separating targeted therapeutic minicells from the minicell-producing parent cells, thereby generating a composition comprising targeted therapeutic minicells. In some embodiments, the method further comprises inducing targeted therapeutic minicell formation from a culture of minicell-producing parent cells. In some embodiments, the method further comprises inducing expression of the gene encoding the genetic suicide endonuclease. In some embodiments, targeted therapeutic minicell formation is induced by the presence of one or more chemical compounds selected from isopropyl β-D-1-thiogalactopyranoside (IPTG), rhamnose, arabinose, xylose, fructose, melibiose, and tetracycline. In some embodiments, the expression of the gene encoding the genetic suicide endonuclease is induced by a change in temperature. In some embodiments, the method further comprises purifying the targeted therapeutic minicells from the composition. In some embodiments, the targeted therapeutic minicells are substantially separated from the parent cells by a process selected from the group including but not limited to centrifugation, filtration, ultrafiltration, ultracentrifugation, density gradient(s), immunoaffinity, immunoprecipitation, and any combination of the preceding purification methods. In some embodiments, targeted therapeutic minicells are lyophilized. In some embodiments, targeted therapeutic minicells are frozen. In some embodiments, targeted therapeutic minicells are lyophilized and then frozen. In some embodiments, targeted therapeutic minicells are formulated as a frozen suspension in a cryoprotectant excipient or other pharmaceutically acceptable carrier or GRAS substance. In some embodiments, targeted therapeutic minicells are exposed to ionizing irradiation. In some embodiments, targeted therapeutic minicells are terminally sterilized by exposure to ionizing irradiation. In some embodiments, targeted therapeutic minicells are terminally sterilized by exposure to ionizing gamma irradiation.

Further embodiments provide immunomodulatory, immunogenic, and targeted therapeutic minicells comprising an outer membrane, where the lipopolysaccharide constituents of the outer membrane comprises Lipid A molecules having no myristoyl moiety ("detoxified lipopolysaccharide" or "detoxified LPS"). Detoxified LPS results in the reduction of pro-inflammatory immune responses in a mammalian host compared to the inflammatory response induced by the outer membrane of eubacterial minicells that are derived from a corresponding wild-type bacterium.

1. Minicell Production

Minicells are achromosomal, membrane-encapsulated biological nanoparticles (approximately 250-500 nm in diameter depending on the strain type and growth conditions used) that are formed by bacteria following a disruption in the normal cell division apparatus. In essence, minicells are small, metabolically active replicas of normal bacterial cells with the exception that they contain no chromosomal DNA and as such, are non-dividing and non-viable. Although minicells do not contain chromosomal DNA, plasmid DNA, RNA, native and/or recombinantly expressed proteins, and other metabolites have all been shown to segregate into minicells. Minicells can be made from a litany of bacterial species and strains including but not limited to *Escherichia* spp., *Salmonella* spp., *Shigella* spp., *Vibrio* spp., *Neisseria* spp., *Campylobacter* spp., *Pseudomonas* spp., *Yersinia* spp., *Chlamydomonas* spp., *Acinetobacter* spp., *Listeria* spp., *Bacillus* spp., *Haemophilus* spp., *Clostridium* spp., *Francisella* spp., *Rickettsia* spp., and others.

Disruption in the coordination between chromosome replication and cell division lead to minicell formation from the polar region of most rod-shaped prokaryotes. Disruption of the coordination between chromosome replication and cell division can be facilitated through the over-expression of some of the genes involved in septum formation and binary fission. Alternatively, minicells can be produced in strains that harbor mutations in genes involved in septum formation and binary fission. Impaired chromosome segregation mechanisms can also lead to minicell formation as has been shown in many different prokaryotes.

Similarly, minicell production can be achieved by the over-expression or mutation of genes involved in the segregation of nascent chromosomes into daughter cells. For example, mutations in the parC or mukB loci of *E. coli* have been demonstrated to produce minicells. Both affect separate requisite steps in the chromosome segregation process in Enterobacteriacea. It can be assumed that like the cell division genes described above, manipulation of wild type levels of any given gene involved in the chromosome segregation process that result in minicell production will have similar effects in other family members.

Because the cell division and chromosome replication processes are so critical to survival, there exists a high level of genetic and functional conservation amongst prokaryotic family members with respect to genes responsible for these processes. As a result, the over-expression or mutation of a cell division gene capable of driving minicell production in one family member can be used to produce minicells in another. For example, it has been shown that the over-expression of the *E. coli* ftsZ gene in other Enterobacteriacea family members such as *Salmonella* spp. and *Shigella* spp as well as other class members such as *Pseudomonas* spp. will result in similar levels of minicell production.

The same can be demonstrated in the mutation-based minicell producing strains of the family Enterobacteriacea. For example, deletion of the min locus in any of Enterobacteriacea family members results in minicell production. Cell division genes from the Enterobacteriacea in which mutation can lead to minicell formation include but are not limited to the min genes (MinCDE). While minicell production from the min mutant strains is possible, these strains have limited commercial value in terms of being production strains for minicell-based biopharmaceuticals. Strains with deletions or mutations within the min genes make minicells at constitutively low levels, presenting problems in terms of commercialization and economies of scale as well as severely limiting the use of recombinant expression technology to generate the bioactive molecules intended for delivery. Minicell yields from the min mutant strains are relatively low, which can increase production cost and/or scale required to generate sufficient numbers of minicells to support market demand for a given biopharmaceutical. Moreover, deletion(s) in the min locus impart constant selective pressure on these strains and the spontaneous generation of compensatory suppressor mutations can lead to a loss of minicell-producing phenotype. This eventuality can have potential negative impact upon minicell yield. Additionally, using cell division mutant strains to produce minicells that encapsulate biologically active molecules that are recombinantly expressed by the minicell-producing parent cells (such as proteins, RNA, DNA, and other catabolites for diagnostic or therapeutic delivery) is problematic. Because the onset of minicell production in the mutant strains cannot be controlled and occurs at a constitutively low level, taking the approach of using the parental cells to recombinantly generate bioactive molecules intended for delivery results in an inconsistent product where some minicells will contain no biologically active molecules (i.e. minicells were made before recombinant expression), while others will contain widely variable amounts of biologically active molecules. In summary, the shortcomings of mutation-based minicell-producing strains can lead to manufacturing complications that may limit their utility in minicell production for commercial purposes.

Minicell-producing strains that overexpress cell division genes ("overexpressers") are preferred over mutation-based strains because the minicell-production phenotype is controllable as long as the cell division genes to be overexpressed are placed under the control of an inducible or other conditionally active eubacterial promoter system. Minicell production from strains overexpressing the cell division gene ftsZ were discovered by researchers who were identifying essential cell division genes in *E. coli* using plasmid-based complementation studies. In these studies, the ftsZ gene was present in over 10 copies per cell. The presence of multiple gene copies of ftsZ was demonstrated to produce minicells and extremely long filamented cells. Ultimately, this transition into the irreversible filamentous phenotype negatively impacts minicell yields from strains overexpressing ftsZ from multi-copy plasmids, although the number of minicells produced is still higher than that of any mutant strain. It has since been demonstrated that by reducing the number of ftsZ gene copies to a single, chromosomal duplication, the number of minicells produced increases over those strains where ftsZ is located on multi-copy plasmids and that the filamentous phenotype is less profound. Thus, one of the preferred composition(s) comprises minicell-producing strains that inducibly overexpress the ftsZ gene from a duplicate, chromosomally integrated copy of ftsZ. The duplicate ftsZ gene used can be derived directly from the species of bacteria in which the minicell-production phenotype is being engineered and can also be derived from the ftsZ gene sequence from other species of bacteria. By way of non-limiting example, overexpression of the ftsZ gene of *Escherichia coli* can be used to generate minicells from *Escherichia coli* and *Salmonella typhimurium*. Resulting strains are comprised of the wild type ftsZ gene and a separate, duplicative, and inducible copy of the ftsZ gene on the chromosome and the inducible genetic suicide mechanism(s) described in U.S. patent publication No. 2010/0112670, which is incorporated herein by its entirety. By way of non-limiting example, division genes that can be over-expressed to produce minicells in the family Enterobacteriaceae include but are not limited to ftsZ, minE, sulA, ccdB, and sfiC. The preferred composition is to have a duplicate copy(s) of a cell division gene(s) under the control of an inducible promoter that is stably integrated into the chromosome of a given eubacterial strain. It is easily recognized by one skilled in the art that this same strategy could be imparted if the inducible cell division gene cassette were present on a plasmid, cosmid, bacterial artificial chromosome (BAC), recombinant bacteriophage or other episomal DNA molecule present in the cell.

This inducible phenotype approach to minicell production has several distinct advantages over the mutant systems. The first is that because there are no constitutive genetic mutations in these strains, there exists no selective pressure during normal growth and the cells of the culture maintain a very stable and normal physiology until the minicell phenotype is induced. The end result is that inducible minicell producing strains are healthier and more stable, which ultimately results in higher yields of minicells. Another distinct advantage of using the inducible phenotype approach to minicell production is in cases where minicells are to be used to deliver biologically active molecules such as proteins, therapeutic RNAs, plasmid DNAs, and other bioactive catabolites where these molecules are recombinantly expressed by the minicell-producing parent cells prior to (pre-induction) or during the induction (co-induction) of the minicell-producing phenotype, such that the minicells that are produced encapsulate those recombinant biologically active molecules. In these cases, the preferred method is to induce the formation of the biologically active molecule(s) within the parental cells prior to inducing the minicell phenotype, so that all of the minicells produced will contain the desired amount of the biologically active molecule(s). Alternatively, the minicells themselves are capable of producing the bioactive molecule after being separated from the parental cells. This includes but is not limited to forming the bioactive molecule from an episomal nucleic acid or RNA encoding for the bioactive molecule located within the minicell or by preexisting protein constituents of minicells after being separated from the parental cells. Any of these expression strategies can be employed to express and/or display binding moieties on the surfaces of minicells. These advantages, when used in combination, result in a higher quality and quantity of minicells. In addition, these minicells can further comprise small molecule drugs that can be loaded into minicells as described in more detail below.

2. Minicell Purification

Because minicells are derived from some bacteria that are pathogenic or opportunistically pathogenic, it is important that any contaminating parental cells be functionally eliminated from a given population before administration as a biopharmaceutical product. Any or all of the methodologies disclosed herein can be used alone or in combination to purify minicells prior to terminal sterilization by ionizing irradiation.

Conventionally, live parental cells have been eliminated through either physical means or biological means or both. Physical means include the use of centrifugation-based separation procedures, filtration methodologies, chromatography methodologies, or any combination thereof. Biological elimination is achieved by but not limited to the preferential lysis of parental cells, the use of auxotrophic parental strains, treatment with antibiotics, treatment with UV irradiation, essential metabolite deprivation including but not limited to diaminopimelic acid (DAP) deprivation, selective adsorption of parental cells, treatment with other DNA damaging agents, and induction of a suicide gene.

Preferential lysis of parental cells is typically mediated by inducing the lytic cycle of a lysogenic prophage. In the case of minicell producing strains, it is most useful to use a prophage that is lysis competent but defective at re-infection, such that minicells are not subsequently infected and lysed during activation of the lytic phenotype. Alternatively, and by way of non-limiting example, individual genes such as those classified as members of the holin gene family, can be expressed to achieve similar levels of lysis without the concerns over re-infection inherent to the use of lysogenic prophages. Both approaches are limited by the fact that the lysis event, regardless of the method used to achieve it, expels unacceptable amounts of free endotoxin into the media. Removal of such large amounts of free endotoxin is difficult, time consuming, suffers from lot to lot variability, and is ultimately cost prohibitive.

The use of auxotrophic strains raises concerns over reversion and as such can only be used in cases where minicells are to be produced from commensal or non-pathogenic strains of bacteria. Thus, their application is limited with respect to being used as a method for elimination of live non-pathogenic parental cells used in minicell production.

Treatment with UV irradiation can be useful in the elimination of live parental cells on a minicell production run with the exception in some embodiments that UV irradiation is random with respect to its effects on nucleic acids and results are highly variable from lot to lot. In some embodiments, UV irradiation is not used when minicells are used to deliver therapeutic or prophylactic nucleic acids as UV irradiation randomly damages all nucleic acids. For instance, plasmid DNA may be highly susceptible to DNA damage by UV irradiation and may be rendered ineffective although still effectively delivered by minicells.

Diaminopimelic acid (DAP) deprivation can be useful in the elimination of live parental cells with the exception that this approach is limited by the number of species it can be used for. In other words, not all parent cell species capable of producing minicells require DAP for survival. DAP mutants in *E. coli* minicell-producing strains are of great advantage and in some cases preferred over the wild type. The advantage of using DAP is that this compound (diaminopimelic acid, an *E. coli* cell wall constituent) is critical for the growth of *E. coli* and is not present in or produced by animals. Thus, should a "viable" *E. coli* minicell-producing parental cell be administered along with targeted minicells, the parental cell will be unable to grow and will thereby be inert to the animal and with respect to minicell activity. A similar approach can be used with *Salmonella* spp. based minicell-producing parental strains except in that case the aro genes, preferably aroB are removed.

Selective adsorption methodologies have yet to be explored with respect to purifying minicells from viable parental cells. Selective adsorption is defined as any process by which parental cells or minicells are preferentially adsorbed to a substrate by virtue of their affinity for the substrate. By way of non-limiting example, high affinity protein-protein interactions could be exploited for this use. By way of non-limiting example, the novel minicell outer membrane protein Lpp-OmpA::Protein A has a high affinity for the Fc region of most antibodies. The gene encoding for Lpp-OmpA::Protein A is under the control an inducible promoter could easily be introduced on to the chromosome of a minicell producing strain. Minicells could be produced from this strain prior to the activation of expression of the Lpp-OmpA::ProteinA gene such that the minicells produced do not express or display Lpp-OmpA::Protein A on their cell surface. Once the desired quantity of minicells is produced from the strain, the viable cells within the culture could be given the signal to produce the Lpp-OmpA::Protein A protein such that Lpp-OmpA::Protein A is only expressed and displayed upon viable cells. Once Lpp-OmpA::Protein A is preferentially expressed on the surface of viable parental cells, they can be easily adsorbed to a substrate coated with antibodies or other Fc-region containing proteins. Once adsorbed, minicells can be selectively purified away from viable parental cells by a number of different means dependent upon the substrate type used. Substrates include but are not limited to solid-phase chromatographic columns used in gravity filtration applications, magnetic beads, ion exchange columns, or HPLC columns.

In some embodiments, minicells are substantially separated from the minicell-producing parent cells in a composition comprising minicells. For example, after separation, the composition comprising the minicells is more than about 99.99%, 99.95%, 99.9%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 65%, 60%, 55%, 50%, 45%, 40%, 35% or 30% free of minicell-producing parent cells. In some embodiments, the composition contains less than about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% minicell-producing parent cells prior to sterilization by ionizing irradiation.

In some embodiments, it is advantageous for the final composition to contain few enough contaminating parental cells, viable or otherwise, so as not to be too toxic or interfere with the activity of targeted minicells when administered in vivo for therapeutic purposes.

3. Targeting Minicells to Specific Cells, Tissues, and Organs

Minicell-based biopharmaceutical products that have been terminally sterilized by exposure to ionizing irradiation can be utilized to target and deliver bioactive molecules or otherwise exert their immunomodulatory, immunogenic, and therapeutic properties upon a specific receptor, protein, nucleic acid, cell, tissue, and organ types using several approaches. Minicell-targeting strategies include, but are not limited to, two categories. The first is the use of minicells derived from bacterial species that have a natural affinity or tropism for particular cells, tissues, or organs of interest. The second approach is to engineer minicells to target a specific receptor, protein, nucleic acid, cell, tissues, and organs of choice. This second approach can be further divided into, for examples, two broad categories that include either: (i) the recombinant expression and surface display of exogenous polypeptide targeting proteins or, (ii) the incorporation of exogenously added targeting moieties to minicell surfaces. Non-limiting applications and utility of these approaches are described in more details herein.

As appreciated by those skilled in the art, minicells can be made from various bacterial species and strains including but not limited to *Escherichia* spp., *Salmonella* spp., *Shigella* spp., *Vibrio* spp., *Neisseria* spp., *Campylobacter* spp., *Pseudomonas* spp., *Yersinia* spp., *Chlamydia* spp., *Acinetobacter* spp., *Listeria* spp., *Bacillus* spp., *Haemophilus* spp., *Clostridium* spp., *Francisella* spp., and *Rickettsia* spp. Many of these species and strains of bacteria have natural tropism for distinct receptor, protein, nucleic acid, cell, tissue, and organ types. Minicells derived from these bacterial species and strains with natural tropism for distinct receptor, protein, nucleic acid, cell, tissue, and organ types have the same tropism and target the same distinct receptor, protein, nucleic acid, cells, tissues, and organs as the viable chromosome containing parental cells from which they are derived.

Minicells can be engineered, for example, to preferentially target particular cell types through recombinant expression and minicell-surface display of cell-specific targeting moieties. This approach includes the use of bacterial membrane protein fusion and display technologies as well as the expression of heterologous bacterial adhesin and other bacterial cell attachment or invasin molecules. In the case of the former, minicells are engineered to express and/or display an outer membrane protein fused to a cell targeting polypeptide such that the cell-targeting polypeptide is displayed on the minicell surface in sufficient quantities as to confer cell-specific targeting properties to said minicell. Such outer membrane proteins with which cell targeting polypeptides may be fused and displayed on the minicell surface include but are not limited to Lpp-OmpA, LamB, TraA, OmpC, OmpF, FliC, FliD, IgAP, fimbrae proteins and pilus proteins. Targeting polypeptides to be fused and displayed include but are not limited to single chain antibody fragments (scFv) specific for eukaryotic cell membrane proteins, eukaryotic receptor ligands (EGF, VEGF, PDGF, etc.), and non-naturally occurring targeting polypeptides arrived at through orthogonal screening technologies such as phage display. The recombinant expression of bacterial cell-surface localized adhesin and invasin proteins is also utilized to confer cell-specific targeting properties to minicells. In this case, bacterial adhesins with natural specificity for eukaryotic cell membrane proteins are recombinantly expressed and displayed on the minicell surface in quantity sufficient to confer preferential targeting of minicells to eukaryotic cells expressing said membrane protein. Examples of bacterial adhesins and invasin molecules include but are not limited to Invasin from *Yersinia pseudo-tuberculosis*, FimH from *Escherichia coli*, Internalin A, Internalin B, and Type IV Pilus.

Minicells can be engineered to preferentially target particular cell types through the coupling of cell-specific targeting moieties onto the minicell surface using either non-covalent or covalent coupling technologies. Covalent coupling technologies incorporate the use of chemical cross-linkers to attach a wide variety of targeting moieties to the surface of minicells. Such moieties include but are not limited to polypeptides, nucleic acids, and small molecules and cross-linking reagents appropriate for each are easily selected for each moiety type by those skilled in the art. Cross-linking reagents include but are not limited to those listed in Table 1. Preferred targeting moieties to be covalently attached to the minicell surface include but are not limited to antibodies and antibody derivatives. Antibody derivatives include but are not limited to Fc, Fab, single heavy or light chains, and any other antibody derivative wherein the variable region and complementarity determining regions are functional with respect to their conferring specificity for a particular epitope. Other types of targeting moieties that are employed include receptor-specific polypeptide ligands (e.g. growth factors), receptor-specific hormone ligands, and aptamers.

Table 1 lists non-limiting types of chemical cross-linking reagents used to conjugate different targeting molecules onto the minicell surface, along with a description of which cross-linkers are best suited for different purposes. As listed in the table, many of the chemical cross-linkers can also be utilized to generate bispecific antibody-based targeting molecules that may be placed on the minicell surface for the purposes of rendering said minicells capable of targeting a particular cell, tissue, or organ type. In cases where cross-linkers are used to covalently link targeting molecules directly to the minicell surface, the targeting molecule, preferably an antibody or antibody derivative, is functionalized per the specifications provided in the cross-linker manufacturer's product insert in one reaction, while minicells to be coupled are functionalized per the manufacturer's further specifications in a separate reaction (typically a treatment with a reducing agent such as dithiothreitol, 2-beta mercaptoethanol, or tris(2-carboxyethyl)phosphine). For example, the functionalized targeting moiety and the functionalized minicells can then be mixed together, preferably at a molar ratio of greater than 1 targeting molecule to 1 minicell, and allowed to incubate to complete the coupling reaction as per the specifications in the cross-linker manufacturer's product insert(s). In some embodiments, following a pair of brief wash steps (e.g., pelleting minicells and resuspending targeted minicells in a buffered solution, preferably phosphate-buffered saline) targeted minicells can then be further loaded with small molecule drugs or small nucleic acid payloads by co-incubation with either or both at room temperature or 4° C. for 2-24 hours. In some embodiments, following incubation, excess drug and small nucleic acids are washed away (again by pelleting and resuspending) and targeted, payload-containing minicells are formulated in a pharmaceutically acceptable excipient, preferably a GRAS substance in a pharmaceutical grade diluent. In some embodiments, following resuspension in pharmaceutically acceptable excipient (for example, D-trehalose in sterile water for injection), minicells can be placed in individual sealed, stoppered vials and stored as a frozen suspension or further lyophilized and the lyophile stored frozen. Vials containing minicells as a lyophile or frozen suspension can then be terminally sterilized by exposure to ionizing irradiation and stored frozen until use.

TABLE 1

Non-limiting chemical cross-linker types that can be used
to attach targeting moieties to bacterial minicells

| Cross-linking target(s) | Cross-linking reagent(s) | Purpose(s) |
|---|---|---|
| Amine to amine (homobifunctional) | disuccinimidyl glutarate (DSG), disuccinimidyl suberate (DSS), bis(sulfosuccinimidyl)suberate (BS3), tris(succinimidyl)aminotriacetate (TSAT), BS(PEG)5, BS(PEG)9, Lomant's reagent (DSP), 3,3'-dithiobis(sulfosuccinimidylpropionate) (DTSSP), disuccinimidyl tartrate (DST), Bis[2-(succinimidooxycarbonyloxy)ethyl]sulfone (BSOCOES), ethylene glycol bis[succinimidylsuccinate] (EGS), ethylene glycol bis[sulfosuccinimidylsuccinate] (Sulfo-EGS), dimethyl adipimidate (DMA), dimethyl pimelimidate (DMP), dimethyl suberimidate (DMS), dimethyl 3,3'-dithiobispropionimidate (DTBP), 1,5-difluoro-2,4-dinitrobenzene (DFDNB) | Used to cross-link polypeptides, peptides, DARPins, and other amine-containing targeting molecules containing amine groups to exposed external regions of minicell outer membrane proteins also containing amines. |
| Sulfhydryl to sulfhydryl (homobifunctional) | Maleimides (BMOE, BMB, BMH, TMEA, BM[PEG]2, BM[PEG]3, BMBD, and DTME), Pyridyldthiols (DPDPB), vinylsulfone | Used to cross-link polypeptides, peptides, DARPins, and other amine-containing targeting molecules containing naturally occurring or recombinantly engineered cysteine residues (contain sulfhydryls) with minicell to exposed external regions of minicell outer membrane proteins also containing cysteine residues (contain sulfhydryls). |
| Non-selective (homobifunctional) | Bis-[b-(4-Azidosalicylamido)ethyl]disulfide (BASED) | Used to cross-link polypeptides, peptides, DARPins, amine-containing conjugates, carbohydrates, aptamers, nucleic acids, and hormones in non-selective fashion to minicells. |
| Amine to sufhydryl (heterobifunctional) | N-(a-Maleimidoacetoxy) succinimide ester (AMAS), BMPS, GMBS, Sulfo-GMBS, MBS, Sulfo-MBS, Succinimidyl-4-(N-maleimidomethyl)cyclohexane-1-carboxylate (SMCC), Sulfosuccinimidyl-4-(N-maleimidomethyl)cyclohexane-1-carboxylate (Sulfo-SMCC), EMCS, Sulfo-EMCS, SMPB, Sulfo-SMPB, SMPH, LC-SMCC, Sulfo-KMUS, SM(PEG)2, SM(PEG)4, SM(PEG)6, SM(PEG)8, SM(PEG)12, SM(PEG)24, SPDP, LC-SPDP, Sulfo-LC-SPDP, SMPT, Sulfo-SMPT, SIA, SBAP, SIAB, Sulfo-SIAB, | Used to cross-link polypeptides, peptides, DARPins, and other amine-containing targeting molecules via naturally occurring or recombinantly engineered cysteine residues (contain sufhydryls) to exposed external regions of minicell outer membrane proteins containing amines. Conversely, used to cross-link polypeptides, peptides, DARPins, and other cysteine-containing amines to exposed external regions of minicell outer membrane proteins containing cysteines (contain sulfhydryls). |

TABLE 1-continued

Non-limiting chemical cross-linker types that can be used
to attach targeting moieties to bacterial minicells

| Cross-linking target(s) | Cross-linking reagent(s) | Purpose(s) |
|---|---|---|
| Amine to non-selective | N-Hydroxysuccinimidyl-4-azidosalicylic acid (NHS-ASA), ANB-NOS, Sulfo-HSAB, Sulfo-NHS-LC-ASA, SANPAH, Sulfo-SANPAH, Sulfo-SFAD, Sulfo-SAND, Sulfo-SAED, succinimidyl-diazirine (SDA), Sulfo-SDA, LC-SDA, Sulfo-LC-SDA | Used to cross-link polypeptides, peptides, DARPins, and other amine-containing targeting molecules via naturally occurring or engineered amine groups to minicell surface-localized membrane proteins. |
| Amine to carboxyl | Carbodiimides (dicyclohexylcarbodiimide [DCC], 1-Ethyl-3-[3-dimethylaminopropyl]carbodiimide hydrochloride [EDC or EDAC]) | Used to cross-link polypeptides, peptides, DARPins, and other amine-containing targeting molecules to exposed external regions of minicell outer membrane proteins containing exposed naturally occurring or recombinantly engineered carboxyl termini. Conversely, used to cross-link polypeptides, peptides, DARPins, and other targeting molecules via their carboxyl termini to exposed external regions of minicell outer membrane proteins containing amines. |
| Sulfhydryl to non-selective | Pyridyldithiol/Aryl Azide (ADPD) | Used to cross-link polypeptides, peptides, DARPins, and other sulfhydryl-containing targeting molecules to minicells. Conversely, used to cross-link polypeptides, peptides, DARPins, and other targeting molecules to exposed regions of minicell outer membrane proteins containing cysteines (contain sulfhydryls) |
| Sulfhydryl to carbohydrate | Maleimide/Hydrazide, BMPH, 3,3'-N-[e-Maleimidocaproic acid] hydrazide, trifluoroacetic acid salt (EMCH), MPBH, KMUH | Used to cross-link sulfhydryl containing targeting molecules to to carbohydrates on surfaces of minicells. Conversely, used to cross-link glycosylated (contain carbohydrate) targeting molecules to exposed regions of minicell outer membrane proteins containing cysteine residues (contain sulfhydryls). |

TABLE 1-continued

Non-limiting chemical cross-linker types that can be used to attach targeting moieties to bacterial minicells

| Cross-linking target(s) | Cross-linking reagent(s) | Purpose(s) |
|---|---|---|
| Hydroxyl to sulfydryl | Isocyanate/Malemide (PMPI) | Used to cross-link sulfhydryl containing targeting molecules to minicell surfaces containing free hydroxyls. |

Antibodies can be used to aid in the targeting of minicells to a specific tissue, organ, and cell type involved in the cause, progression, maintenance, or manifestation of disease can be derived from or be part of any immunoglobulin or immunoglobulin subclass, including but not limited to IgA, IgM, IgD, IgG, and IgE. Antibodies of any subclass intended to facilitate the targeting function of minicells can be "humanized", although any antibody of any subclass against a cell specific antigen can be raised in any animal known to generate antibody responses through adaptive immunity to achieve the same goal. In nature, antibodies are generated such that they contain two separate arms (Fab's), each of which recognizes the same epitope of a particular antigen. However, as described below, advances in molecular biology have enabled researchers to modify the specificity of each arm (or in some cases the Fc region of the molecule) to recognize distinctly different epitopes that may or may not occur in the same or different antigens. These antibody derivatives are referred to as a 'bispecific' antibodies or 'bispecific' targeting moieties.

In the laboratory, antibodies can be engineered to be independently specific for different antigens, such that a single antibody targets two separate antigens simultaneously. By way of non-limiting example, antibodies can be recombinantly engineered to recognize putative surface components of a given eubacterial minicell (e.g., LPS O-antigens or porin proteins) on one Fab' and the other Fab' of the bispecific antibody can be engineered to recognize a eukaryotic cell-specific surface antigen. In another non-limiting variation on this theme, the Fc region of the heavy chains of the antibody can be genetically engineered to specifically bind to a particular epitope within a given antigen (e.g., LPS) while the Fab' portions of the molecule recognize a different epitope in a separate eukaryotic cell-specific surface antigen or vice versa. This same approach to generating bispecific antibodies by recombinant means can be taken with diabodies, triabodies, tetrabodies, Bis-scFv, Fab$_2$, and minibodies, each of which can be engineered to contain one arm specific for a minicell surface molecule and the other for an antigen or receptor on a target eukaryotic cell.

Additionally, those of skill in the art will readily recognize that two separate antibodies, with separate specificities, can be non-covalently attached by coupling them to soluble Protein A, Protein G, or Protein A/G (or any other binding molecule that will recognize and bind two or more antibodies) to form a bispecific antibody derivative capable of adhering to the surface of minicells wherein one antibody within the complex specifically adheres to the surface of the minicell and the other antibody is displayed to specifically recognize and thereby "target" a specific cell, tissue, or organ type expressing an eukaryotic cell-specific surface antigen in vivo. Similarly, one skilled in the art will recognize that two separate antibodies, with separate specificities, can be covalently linked using myriad cross-linking techniques to achieve the same effect.

Non-covalent attachment of targeting moieties includes the use of bi-specific ligands and bi-specific antibodies wherein one portion of the bi-specific ligand or bi-specific antibodies recognize the minicell surface and another portion of the bi-specific ligand or antibodies recognize a eukaryotic cell membrane protein. Bi-specific antibodies and antibody derivatives are defined as those that contain one or more complementarity determining regions (CDR) specific for a minicell surface molecule and one or more CDR(s) specific for a eukaryotic cell. Non-limiting examples of bi-specific antibodies and bi-specific antibody derivatives suitable for use in the methods and compositions disclosed herein are shown in FIG. 1. Bi-specific ligands can, in some embodiments, contain one or more portions specific for the minicell surface and another specific for a eukaryotic cell. One of the preferred methods of non-covalent attachment of antibodies and other ligands to minicells is described in WO/2012/112,696, which is incorporated herein in its entirety by way of reference. The technology described in WO/2012/112,696 utilizes an approach of displaying an Fc-binding region of Protein A or Protein G on the minicell surface by way of a fusion protein and coupling those minicells to an Fc region-containing antibody or other polypeptide ligand to confer targeting properties to said minicells.

As illustrated in FIG. 1, various types of multivalent antibody derivative subtypes commonly recognized in the art can be used to generate targeted minicells. In each non-limiting example illustrated in Example 1, at least one arm of the antibody derivative(s) used is specific for one or more minicell surface structures including but not limited to porin proteins, flagella, pilus, and O-antigen, while the one or more of the additional arms is specific for one or more eukaryotic targets. Bi-specific antibodies made utilizing a cross-linker (bispecific (mab)$_2$ and bispecific F(ab')$_2$) are generated utilizing any of the appropriate members of those listed in FIG. 1, especially with SPDP or any of its listed derivatives. Other multivalent antibody types shown are made using established recombinant, selection, purification, and characterization techniques commonly known to the skilled artisan.

In applications where covalent and non-covalent attachment of antibodies or other targeting moieties are utilized, it is preferable but not mandatory to first purify minicells from parental cells prior to coupling of targeting moieties. As described in more detail below, purified minicells either already contain their respective therapeutic, immunomodulatory, and immunogenic payload at the time of purification, or payloads are added to minicells following purification. In some instances, it is desirable to use a combination of both of these approaches. In the context of the latter two scenarios, targeting moieties may be added prior to or following the addition of exogenous payload(s) to minicells at the discretion of the skilled artisan. The final minicell composition is then further processed and prepared for terminal sterilization by ionizing irradiation.

The antibody, antibody derivative, or other targeting molecule on the surface of targeted therapeutic minicells can preferentially recognize but is not limited to recognizing cell-specific surface antigens including but are not limited to α3β1 integrin, α4β1 integrin, α5β1 integrin, $α_v β3$ integrin, $α_v β1$ integrin, β1 integrin, 5T4, CAIX, CD4, CD13, CD19, CD20, CD22, CD25, CD30, CD31, CD33, CD34, CD40, CD44v6, CD45, CD51, CD52, CD54, CD56, CD64, CD70, CD74, CD79, CD105, CD117, CD123, CD133, CD138, CD144, CD146, CD152, CD174, CD205, CD227, CD326, CD340, Cripto, ED-B, GD2, TMEFF2, VEGFR1, VEGFR2, FGFR, PDGFR, ANGPT1, TIE1, TIE2, NRP1, TEK (CD202B), TGFβR, Death Receptor 5 (Trail-R2), DLL4, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, FAP, GPNMB, ICAMs, VCAMs, PSMA, HER-2/neu, IL-13R alpha 2, MUC-1, MUC16, EGFR1 (HER-1), EGFR2 (HER-2/neu), EGFR3 (HER-3), IGF-1R, IGF-2R, c-Met (HGFR), Mesothelin, PDGFR, EDGR, TAG-72, transferrin receptor, EpCAM, CTLA-4, PSMA, tenascin C, alpha-fetoprotein, vimentin, C242 antigen, TRAIL-R1, TRAIL-R2, CA-125, GPNMB, CA-IX, GD3 ganglioside, RANKL, BAFF, IL-6R, TAG-72, HAMA, and CD166.

In some embodiments, the targeting moiety is selected, in part, because the binding of the minicell-surface displayed antibody targeting moiety, antibody derivatives, and/or other targeting molecules specific for the antigen induce internalization of the targeted minicell, facilitating intracellular payload delivery. Previously described target-specific antibodies that are used as the targeting component, in some embodiments, include but are not limited to mAb 3F8, mAb CSL362, mAb CSL360, mAb J591, Abagovomab, Abciximab, Adalimumab, Afelimomab, Afutuzumab, Alacizumab, ALD518, Alemtuzumab, Altumomab, Anatumomab, Anrukinzumab, Apolizumab, Arcitumomab, Aselizumab, Atlizumab, Atorolimumab, Bapineuzmab, Basiliximab, Bavituximab, Bectumomab, Belimumab, Benralizumab, Bertilimumab, Besilesomab, Bevacizumab, Biciromab, Bivatuzumab, Blinatumomab, Brentuximab, Briakinumab, Canakinumab, Cantuzumab, Capromab, Catumaxomab, CC49, Cedelizumab, Certolizumab, Cetuximab, mAb528, Citatuzumab, Cixutumumab, Clenoliximab, Clivatuzumab, Conatumumab, CR6261, Dacetuzumab, Daclizumab, Daratumumab, Denosumab, Detumomab, Dorlimomab, Dorlixizumab, Ecromeximab, Eculizumab, Edobacomab, Edrecolomab, Efalizumab, Efungumab, Elotuzumab, Elsilimomab, Enlimomab, Epitumomab, Epratuzumab, Erlizumab, Ertumaxomab, Etaracizumab, Exbivirumab, Fanolesomab, Faralimomab, Farletuzumab, Felvizumab, Fezakinumab, Figitumumab, Fontolizumab, Foravirumab, Fresolimumab, Galiximab, Gantenerumab, Gavilimomab, Gemtuzumab, Girentuximab, Glembatumumab, Golimumab, Gomiliximab, Ibalizumab, Irbitumomab, Igovomab, Imciromab, Infliximab, Intetumumab, Inolimomab, Inotuzumab, Ipilimumab, Iratumumab, J591, Keliximab, Labetuzumab, Lebrikizumab, Lemalesomab, Lerdelimumab, Lexatumumab, Libivirumab, Lintuzumab, Lorvotuzumab, Lucatumumab, Lumiliximab, Mapatumumab, Maslimomab, Matuzumab, Mepolizomab, Metelimumab, Milatuzumab, Minretumomab, Mitumomab, Morolimumab, Motavizumab, Muromonab, Nacolomab, Naptumomab, Natalizumab, Nebacumab, Necitutumab, Nerelimomab, Nimotuzumab, Nofetumomab, Ocrelizumab, Odulimomab, Ofatumumab, Olaratumab, Omalizumab, Oportuzumab, Oregovomab, Otelixizumab, Pagibaximab, Palivizumab, Panitumumab, Panobacumab, Pascolizumab, Pemtumomab, Pertuzumab, Pexelizumab, Pintumomab, Priliximab, Pritumumab, PRO140, Rafivirumab, Ramucirumab, Ranibizumab, Raxibacumab, Regavirumab, Resilizumab, Rilotumumab, Rituximab, Robatumumab, Rontalizumab, Rovelizumab, Ruplizumab, Satumomab, Sevirumab, Sibrotuzumab, Sifalimumab, Siltuximab, Siplizumab, Solanezumab, Sonepcizumab, Sontuzumab, Stamulumab, Sulesomab, Tacatuzumab, Tadocizumab, Talizumab, Tanezumab, Taplitumomab, Tefibazumab, Telimomab, Tenatumomab, Teplizumab, TGN1412, Ticilimumab, Tigatuzumab, TNX-650, Tocilizumab, Toralizumab, Tositumomab, Trastuzumab, Tremelimumab, Tucotuzumab, Tuvirumab, Urtoxazumab, Ustekinumab, Vapaliximab, Vedolizumab, Veltuzumab, Vepalimomab, Visilizumab, Volociximab, Votumumab, Zalutumumab, Zanolimumab, Ziralimumab, Zolimomab, and any combination of the preceding.

4. Loading Payloads into Minicells

Eubacterial minicells are capable of encapsulating and delivering several classes of biologically active compounds that have therapeutic, immunomodulatory, immunogenic, and/or diagnostic benefit to an animal, for example a mammal (e.g. a human). Types of biologically active compounds (payloads) that can be delivered by minicells include but are not limited to small molecules (including small molecule drugs), nucleic acids, polypeptides, radioisotopes, lipids, lipopolysaccharides, and any combination thereof. Methods of loading minicells with bioactive payloads include two categories of approaches, and these two categories of approaches may be combined. The first category of approach is by loading exogenous payload(s) into minicells via physical or chemical means. The second category of approach is the recombinant production or expression of the bioactive payload in minicells.

The first method of loading minicells with payload(s) is amenable to but not limited to the loading of exogenous small molecule drugs. As used herein, the term "small molecule" refers to a molecule that has a biological effect and that has a molecular weight of less than 5000 Daltons. In some embodiments, small molecules have a molecular weight of less than 2500 Daltons. In some embodiments, small molecules have a molecular weight of less than 1000 Daltons. In some embodiments, small molecules have a molecular weight of less than 800 Daltons. In some embodiments, small molecules have a molecular weight of less than 500 Daltons. Small molecule drugs include those small molecules that result in pharmacological therapeutic benefit to an animal (including humans).

In some embodiments, small molecules are loaded into minicells by incubating minicells in a high concentration of said small molecule. Over time, small molecules passively diffuse into minicells where they interact with various molecular constituents of minicells thereby becoming entrapped in minicells. Small molecules can be, in some embodiments, released by minicells into target cells once minicells are internalized into endosomes and the degradation/release process ensues.

The species of small molecule drug(s) compatible for use in minicells can be selected from but not limited to antibiotics (anti-infectives, anti-neoplastics, and anti-virals), anti-histamines, and anti-inflammatory pharmacological small molecule agents. Antibiotics (anti-infectives, anti-neoplastics, and anti-virals) that may be used in this context include but are not limited to: (1) DNA damaging agents and agents that inhibit DNA synthesis such as anthracyclines (doxorubicin, daunorubicin, epirubicin), alkylating agents (bendamustine, busulfan, carboplatin, carmustine, cisplatin, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine), platinum derivatives (cisplatin, carboplatin, cis diamminedichloroplatinum), telomerase and topoisomerase inhibitors (Camptosar), (2) microtubule and tubulin binding agents including but not limited to taxanes and taxane derivatives (paclitaxel, docetaxel, BAY 59-8862), (3) anti-metabolites such as capecitabine, chlorodeoxyadenosine, cytarabine (and its activated form, ara-CMP), cytosine arabinoside, dacarbazine, floxuridine, fludarabine, 5-fluorouracil, 5-DFUR, gemcitabine, hydroxyurea, 6-mercaptopurine, methotrexate, pentostatin, trimetrexate, and 6-thioguanine (4) anti-angiogenics (thalidomide, sunitinib, lenalidomide), vascular disrupting agents (flavonoids/flavones, DMXAA, combretastatin derivatives such as CA4DP, ZD6126, AVE8062A, etc.), (5) endocrine therapy such as aromatase inhibitors (4-hydroandrostendione, exemestane, aminoglutethimide, anastrozole, letrozole), (6) anti-estrogens (Tamoxifen, Toremifene, Raloxifene, Faslodex), steroids such as dexamethasone, (7) immuno-modulators such as Toll-like receptor agonists or antagonists, (8) inhibitors to integrins, other adhesion proteins and matrix metalloproteinases), (9) histone deacetylase inhibitors, (10) inhibitors of signal transduction such as inhibitors of tyrosine kinases like imatinib (Gleevec), (11) inhibitors of heat shock proteins, (12) retinoids such as all trans retinoic acid, (13) inhibitors of growth factor receptors or the growth factors themselves, (14) anti-mitotic compounds such as navelbine, vinblastine, vincristine, vindesine, and vinorelbine, (15) anti-inflammatories such as COX inhibitors, (16) cell cycle regulators such as check point regulators and telomerase inhibitors, (17) transcription factor inhibitors, and apoptosis inducers, such as inhibitors of Bcl-2, Bcl-x and XIAP, and any combination of the preceding (1-17).

The second method of loading minicells with therapeutic, immunomodulatory, and immunogenic payloads can be via recombinant expression or production of the payload in minicells. The minicell-producing parental cells can be used to recombinantly express/produce one or more therapeutic, immunomodulatory, and/or immunogenic nucleic acid molecules and/or polypeptides prior to or at the same time that minicells are being produced. Recombinant nucleic acids and/or polypeptides are expressed, segregate into, and are encapsulated by minicells, then delivered to eukaryotic cells by targeted minicells in vivo or in vitro.

Examples of recombinantly expressed/produced therapeutic, immunomodulatory, and/or immunogenic nucleic acids to be delivered by minicells include, but are not limited to, RNA interference molecule(s), or ribozyme(s), double stranded therapeutic RNA (e.g., dsRNA or siRNA), single stranded therapeutic RNA (e.g., shRNA), microRNA, long noncoding RNA, CRISPR RNA, aptamers, ribozymes, eukaryotic expression plasmids encoding for therapeutic polypeptide(s) and/or therapeutic nucleic acids, and any combination of the preceding. Recombinant expression of nucleic acid(s) can be the result of expression from any of the various episomal recombinant prokaryotic expression vectors known in the art including, but not limited to plasmids, cosmids, phagemids, and bacterial artificial chromosomes (BACs), and any combination of the preceding. Recombinant expression can also be achieved by a chromosomally located prokaryotic expression cassette present in one or more copies of the minicell-producing parent cell chromosome. In cases where the nucleic acid molecule(s) to be delivered exert their effects through a "gene silencing" mechanism of action, the nucleic acids are specific for one or more different eukaryotic mRNA transcripts. The nucleic acids can be delivered by the same minicell such that one or more genes are silenced by a single delivery event. Targeted minicells are also used to deliver any of these nucleic acids in combination. In addition, targeted minicells are used to deliver one or more small molecule drugs in concert with one or more nucleic acids.

In cases where the therapeutic nucleic acid molecule(s) is pre-formed by the parental cell by way of recombinant expression from a prokaryotic expression cassette (either chromosomal or episomal in location) and is then packaged inside of the minicells as double stranded RNAs (e.g., siRNA) or single stranded RNAs capable of folding back on themselves to form hairpin structures (e.g., shRNAs), the half-life of the therapeutic RNA(s) within the minicell is increased by use of minicell producing bacterial strains that harbor a deletion or other non-functional mutation in RNase genes (e.g., prokaryotic RNase III) responsible for the degradation of intracellular double stranded and/or hairpin RNA molecules. In the absence of the RNase, the therapeutic RNA molecules accumulate to a higher level, increasing the potency of targeted minicells delivering the therapeutic nucleic acid molecules. In the case of *Escherichia coli* minicell producing strains, mutation or deletions are introduced into the rnc gene, which encodes for the only known somatic RNaseIII in this species.

Recombinantly expressed therapeutic, immunomodulatory, and immunogenic polypeptides to be delivered by targeted minicells include but are not limited to protein toxins, cholesterol-dependent cytolysins, functional enzymes, activated caspases, pro-caspases, cytokines, chemokines, cell-penetrating peptides, vaccine antigens, and any combination of the preceding examples, including conjugates thereof with molecules designed to modulate polarity and/or extend half-life (for example lipids or polyethylene glycol). Recombinant expression of a polypeptide(s) can be the result of expression from any of the various episomal recombinant prokaryotic expression vectors known in the art including but not limited to plasmids, cosmids, phagemids, and bacterial artificial chromosomes (BACs), and any combination of the preceding examples. In similar fashion, recombinant expression can be achieved by a chromosomally located prokaryotic expression cassette present in one or more copies of the minicell-producing parent cell chromosome. The delivery of protein toxins using the targeted minicells of the present application is an advantageous approach in applications where selective elimination of cells in vivo is desirable. Protein toxins which can facilitate endosomal delivery of payloads and/or function as toxic payloads include, but are not limited to, fragments A/B of diphtheria toxin, fragment A of diphtheria toxin, anthrax toxins LF and EF, adenylate cyclase toxin, gelonin, botulinolysin B, botulinolysin E3, botulinolysin C, botulinum toxin, cholera toxin, *clostridium* toxins A, B and alpha, ricin, shiga A toxin, shiga-like A toxin, cholera A toxin, pertussis S1 toxin, perfringolysin O, *Pseudomonas* exotoxin A, *E. coli* heat labile toxin (LTB), melittin, pH stable variants of listeriolysin O (pH-independent; amino acid substitution L461T), thermostable variants of listeriolysin O (amino acid substitutions E247M, D320K), pH and thermostable variants of listeriolysin O (amino acid substitutions E247M, D320K, and L461T), streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, and pyolysin and any combination of the preceding. Cytokines may be recombinantly expressed in and delivered by minicells to impart therapeutic and immunomodulatory effects. Cytokines that may be expressed in and delivered by minicells include but are not limited to Granulocyte Macrophage Colony Stimulating Factor (GMCSF), Tumor Necrosis Factor Alpha (TNF-$\alpha$), Interferon Gamma (IFN-$\gamma$), Interferon Alpha 2b (IFN-$\alpha$2b), Interleukin-2 (IL-2), Interleukin-1a (IL-1a), Interleukin-12 (IL-12), and TRAIL. Vaccine antigens that may be recombinantly expressed and delivered include but are not limited to those encoded for in the genomes of bacterial, viral, and parasitic organisms. Vaccine antigens that may be recombinantly expressed and delivered also include those antigens and neo-antigens present on cancer cells including but not limited to Carcinogenic Embryonic Antigen (CEA), Mesothelin, Mucin-1 (MUC1), BAGE, GAGE, MAGE, SSX, EGFRvIII, Her-2, Gp100, Melan-A/Mart-1, Tyrosinase, PSA, Mammaglobin-A, p53, livin, survivin, beta-catenin-m, HSP70-2/m, HLA-A2-R170J, WT1, PR1, E75, ras, AFP, URLC10, mutant p53, and NY-ESO-1.

Polypeptides can be localized to different sub-cellular compartments of the minicell at the discretion of the skilled artisans. When targeted minicells disclosed herein are derived from a Gram-negative parental minicell-producing strain, recombinantly expressed polypeptides produced therefrom can be localized to the cytosol, the inner leaflet of the inner membrane, the outer leaflet of the inner membrane, the periplasm, the inner leaflet of the outer membrane, the outer membrane of minicells, and any combination of the proceeding. When targeted minicells disclosed herein are derived from a Gram-positive parental minicell-producing strain, recombinantly expressed therapeutic polypeptides produced therefrom can be localized to the cytosol, the cell wall, the inner leaflet of the membrane, the membrane of minicells, and any combination of the proceeding.

In cases where the polypeptide payload(s) is pre-formed by the parental cell by way of recombinant expression from a prokaryotic expression cassette (either chromosomal or episomal in location) and is then packaged inside of the minicells as the payload, the half-life of the polypeptide payload(s) within the minicell is increased by use of minicell producing bacterial strains that harbor a deletion or other non-functional mutation in protease genes (e.g., the lon protease of $E. coli$) responsible for proteolysis. In the absence of the protease(s), the polypeptide payload(s) molecule(s) accumulates to a higher level, increasing the potency of targeted minicells delivering the polypeptide payload molecules. In the case of $Escherichia coli$ minicell producing strains, mutation or deletions can be introduced into one or more of the lon, tonB, abgA, ampA, ampM, pepP, clpP, dcp, ddpX/vanX, elaD, frvX, gcp/b3064, hslV, hchA/b1967, hyaD, hybD, hycH, hycI, iadA, ldcA, ycbZ, pepD, pepE, pepQ, pepT, pmbA, pqqL, prlG, ptrB, sgcX, sprT, tldD, ycaL, yeaZ, yegQ, ygeY, yggG, yhbO, yibG, ydpF, degS, ftsH/hflB, glpG, hofD/hopD, lepB, lspA, pppA, sohB, spa, yaeL, yfbL, dacA, dacB, dacC, degP/htrA, degQ, iap, mepA, nlpC, pbpG, tsp, ptrA, teas, umuD, ydcP, ydgD, ydhO, yebA, yhbU, yhjJ, and nlpD genes.

Effective delivery of therapeutic, immunomodulatory, and immunogenic polypeptides and nucleic acid payloads by way of receptor mediated endocytosis can be limited if the polypeptide(s) and/or nucleic acid(s) delivered are exposed to the protease and nuclease rich environment of the endosomal compartment for too long prior to being released to the cytosol of the targeted eukaryotic cell. Most polypeptides and nucleic acids have no intrinsic ability to escape the endosomal compartment. A few exceptions from the protein toxin family, including the cholesterol dependent cytolysins/toxins (e.g. LLO, perfringolysin O (PFO), and streptolysin O (SLO)) as well as fragment A/B of diphtheria toxin (escape mediated by fragment B), ricin, and $Pseudomonas$ exotoxin A exist. Those protein toxins that do contain intrinsic endosomal escape properties do not necessarily require the co-presence of a separate endosomal disruption component in the targeted minicell to be effective and the decision to include an endosomal disrupting agent is at the discretion of the skilled artisans. Other polypeptides and nucleic acids have no intrinsic ability to escape the endosomal compartment, thus, the skilled artisan would recognize that enhanced endosomal escape of many different therapeutic polypeptides delivered by the endosomal route is desirable. The listeriolysin O (LLO) protein of the intracellular Gram-positive pathogenic bacterium $Listeria monocytogenes$ is capable of being incorporated into those embodiments of the present application that include but are not limited to a polypeptide or nucleic acid payload component or other therapeutic payload requiring endosomal escape to confer best activity. In some embodiments, full length LLO (containing the signal secretion sequence) is used as the endosomal disruption agent. In some embodiments, the signal sequence of LLO (making cLLO) is removed at the genetic level using recombinant techniques known in the art and cLLO is used as the endosomal disruption agent. In some embodiments, thermostable and/or pH-independent versions of LLO (harboring mutations E247M, D320K and/or L461T, sLLOpH) are employed. When expressed in an minicell producing bacterial strain that also expresses therapeutic polypeptide(s) and/or nucleic acid(s), LLO (or any of the LLO variants or other endosomal escape facilitators) can be co-encapsulated with the therapeutic polypeptide(s) and/or nucleic acid(s) within the minicells. Upon targeting of the minicell(s), receptor mediated endocytosis carries the minicell into the endosome. The harsh environment of the endosome begins to degrade the engulfed minicell, co-releasing the payload(s) along with the endosomal disruption agent (e.g., LLO, any of its variants, or other endosomal disrupting agent). The released endosomal disruption agent component then facilitates release of the payload(s) from the endosome into the cytosol where the payload can exert its biological effect(s). In addition to LLO, preferred endosomal disruption agents include other cytolysins, such as PFO and SLO and derivatives thereof, and phospholipases, such as PI-PLC or PC-PLC.

In addition to being used as targeted therapeutic, immunomodulatory, and immunogenic minicells, the minicells disclosed herein can also be used as targeted immunogenic minicell vaccines. Protein antigen and/or DNA vaccine loaded minicells are targeted directly to distinct subsets of antigen presenting cells of the immune system by utilizing antibodies or other minicell-surface displayed molecules that are specific for eukaryotic cell surface markers expressed by these antigen presenting cell subsets. In some embodiments, it can be also desirable but not necessary to include LLO or one of its variants (described above) to facilitate transfer of antigen or DNA vaccine to the eukaryotic cell cytosol to promote MHC class-I loading, which stimulates cellular immunity. It can also be desirable to promote MHC class-II loading to stimulate humoral (antibody mediated) immunity by keeping antigens inside the endosomal compartments where the large majority of MHC class II binding occurs. This can be accomplished by eliminating or decreasing the LLO component of the targeted minicell vaccine. In addition, targeted vaccine minicells are further engineered to either express or be loaded with exogenous adjuvant as deemed appropriate by the skilled artisan. Adjuvants can be general adjuvants (such as Keyhole limpet hemocyanin or complete Freud's adjuvant) or can be targeted molecular adjuvants. Targeted molecular adjuvants include those that are antagonists or agonists of Toll-Like Receptors as well as other cellular constituents that have immunomodulatory properties. Targeted vaccines provide recipient immunity to infectious disease agents including but not limited to those infectious disease agents of bacterial, viral, and parasitic origin(s). Targeted vaccines also provided recipient immunity to tumors and other aberrant disease(s) of autologous nature.

Following the construction and any required characterization of any of the preceding minicell compositions, said minicell compositions are formulated into a pharmaceutical composition, filled into sterile pharmaceutical grade containers, stoppered, sealed, and subjected to terminal sterilization by irradiation.

5. Pharmaceutical Compositions

The present application also relates to compositions, including but not limited to, pharmaceutical compositions. The term "pharmaceutical composition" used herein refers to a mixture comprising at least one excipient, preferably a physiologically acceptable excipient, and one or more minicell compositions. The pharmaceutical composition may further include one or more "diluents" or "carriers".

The term "excipient" as used herein refers to a chemical compound or combination of compounds that does not inhibit or prevent the incorporation of the biologically active peptide(s) into cells or tissues. An excipient is any more or less inert substance that can be added to a composition in order to confer a suitable property, for example, a target concentration of active, suitable consistency, stability and/or to achieve properties in which delivery of the active to the target is facilitated (e.g. a drug formulation). Suitable excipients include, in particular, fillers such as sugars, including lactose, sucrose, mannitol, or sorbitol, glidants, disintegrants, binders, lubricants, polymers (sustained release), cellulose preparations such as, for example, maize starch, wheat starch, rice starch, agar, pectin, xanthan gum, guar gum, locust bean gum, hyaluronic acid, casein potato starch, gelatin, gum tragacanth, methyl cellulose, hydroxypropyl-methyl-cellulose, polyacrylate, sodium carboxymethylcellulose, and/or polyvinylpyrrolidone (PVP), co-solvents such as ethanol, polyethylene glycol, surfactants, antioxidants, preservatives, flavoring agents, complexing agents, lyoprotectants, and cryoprotectants. One preferred excipient in the formulation of minicells to be subjected to terminal sterilization by ionizing irradiation is D-trehalose in sterile water. Although alternative concentrations of D-trehalose or alternative diluents may be used, the preferred concentration of D-trehalose is 12% (w/v) and the preferred diluent is sterile water.

A "diluent" is a pharmaceutically acceptable solvent, for example an aqueous solvent that facilitates dissolution of the composition in the solvent, and it may also serve to stabilize the biologically active form of the composition or one or more of its components. Salts dissolved in water to make buffered solutions are utilized as diluents in the art and preferred diluents are buffered solutions containing one or more different salts. An non-limiting example of preferred buffered solution is phosphate buffered saline (particularly in conjunction with compositions intended for pharmaceutical administration), as it mimics the salt conditions of human blood, although buffered solutions may also be prepared and used at extremes in pH, depending on the route of administration, buffer capacity, and volume of the product administered. Since buffer salts can control the pH of a solution at low concentrations, a buffered diluent rarely modifies the biological activity of a given compound or pharmaceutical composition.

A "carrier" as used herein is an inert substance that allows an active ingredient to be formulated or compounded into a suitable dosage form [e.g., microparticle (e.g., a microsphere), pill, capsule, tablet, solution, colloid, suspension, emulsion, film, gel, cream, ointment; paste, etc.]. A "physiologically acceptable carrier" is a compound suitable for use under physiological conditions that does not abrogate (reduce, inhibit, or prevent) the biological activity and properties of the compound. Preferably, the carrier is a physiologically acceptable carrier, preferably a pharmaceutically or veterinarily acceptable carrier, in which the minicell composition is disposed.

A "pharmaceutical composition" refers to a composition wherein the excipient is a pharmaceutically acceptable excipient, while a "veterinary composition" is one wherein the excipient is a veterinarily acceptable excipient. The term "pharmaceutically acceptable excipient" or "veterinarily acceptable excipient" used herein includes any medium or material that is not biologically or otherwise undesirable, i.e., the excipient may be administered to an organism along with a minicell composition without causing any undesirable biological effects or interacting in a deleterious manner with the complex or any of its components or the organism. Examples of pharmaceutically acceptable excipients are provided in The United States Pharmacopeia, The National Formulary, United States Pharmacopeial Convention, Inc., Rockville, Md. 1990, hereby incorporated by reference herein into the present application. The terms "therapeutically effective amount" and "pharmaceutically effective amount" refer to an amount sufficient to induce or effectuate a therapeutic response in the target cell, tissue, or body of an organism. What constitutes a therapeutically effective amount will depend on a variety of factors, which the knowledgeable practitioner will take into account in arriving at the desired dosage regimen.

If desired, disintegrating agents can also be included, such as cross-linked polyvinyl pyrrolidone, agar, or alginic acid or a salt thereof such as sodium alginate. Other suitable excipients and carriers include hydrogels, gellable hydrocolloids, and chitosan. Chitosan microspheres and microcapsules can be used as carriers. See e.g., WO 98/52547 (which describes microsphere formulations for targeting compounds to the stomach, the formulations comprising an inner core (optionally including a gelled hydrocolloid) containing one or more active ingredients, a membrane comprised of a water insoluble polymer (e.g., ethylcellulose) to control the release rate of the active ingredient(s), and an outer layer comprised of a bioadhesive cationic polymer, for example, a cationic polysaccharide, a cationic protein, and/or a synthetic cationic polymer; U.S. Pat. No. 4,895,724. Typically, chitosan is cross-linked using a suitable agent, for example, glutaraldehyde, glyoxal, epichlorohydrin, and succinaldehyde. Compositions employing chitosan as a carrier can be formulated into a variety of dosage forms, including pills, tablets, microparticles, and microspheres, including those providing for controlled release of the active ingredient(s). Other suitable bioadhesive cationic polymers include acidic gelatin, polygalactosamine, polyamino acids such as polylysine, polyhistidine, polyornithine, polyquaternary compounds, prolamine, polyimine, diethylaminoethyldextran (DEAE), DEAE-imine, DEAE-methacrylate, DEAE-acrylamide, DEAE-dextran, DEAE-cellulose, poly-p-aminostyrene, polyoxethane, copolymethacrylates, polyamidoamines, cationic starches, polyvinylpyridine, and polythiodiethylaminomethylethylene.

The compositions can be formulated in any suitable manner. For example, minicell compositions can be uniformly (homogeneously) or non-uniformly (heterogeneously) dispersed in the carrier. Suitable formulations of minicell composition include, but are not limited to, colloidal solution, dry powder, frozen suspension, liquid suspension and lyophilized formulations. Dry formulations include freeze dried and lyophilized powders, which are particularly well suited for aerosol delivery to the sinuses or lung, or for long term storage followed by reconstitution in a suitable diluent prior to administration. Other preferred dry formulations include those wherein a composition disclosed herein is compressed into tablet or pill form suitable for oral administration or compounded into a sustained release formulation. When the composition is intended for oral administration to be delivered to epithelium in the intestines, it is advantageous in some embodiments that the formulation be encapsulated with an enteric coating to protect the formulation and prevent premature release of the minicell compositions included therein. As those in the art will appreciate, the compositions disclosed herein can be placed into any suitable dosage form. Pills and tablets represent some of such dosage forms. The compositions can also be encapsulated into any suitable capsule or other coating material, for example, by compression, dipping, pan coating, spray drying, etc. Suitable capsules include those made from gelatin and starch. In turn, such capsules can be coated with one or more additional materials, for example, and enteric coating, if desired. Liquid formulations include aqueous formulations, gels, and emulsions.

Some preferred embodiments provide compositions that comprise a bioadhesive, preferably a mucoadhesive, coating. A "bioadhesive coating" is a coating that allows a substance (e.g., a minicell composition) to adhere to a biological surface or substance better than occurs absent the coating. A "mucoadhesive coating" is a preferred bioadhesive coating that allows a substance, for example, a composition to adhere better to mucosa occurs absent the coating. For example, minicells can be coated with a mucoadhesive. The coated particles can then be assembled into a dosage form suitable for delivery to an organism. Preferably, and depending upon the location where the cell surface transport moiety to be targeted is expressed, the dosage form is then coated with another coating to protect the formulation until it reaches the desired location, where the mucoadhesive enables the formulation to be retained while the composition interacts with the target cell surface transport moiety.

Compositions disclosed herein can be administered to any organism, preferably an animal, preferably a mammal, bird, fish, insect, or arachnid. Preferred mammals include bovine, canine, equine, feline, ovine, and porcine animals, and non-human primates. Humans are particularly preferred. Multiple techniques of administering or delivering a compound exist in the art including, but not limited to, ocular, aural, buccal, oral, rectal, (e.g. an enema or suppository), vaginal, transurethral, nasal, pulmonary, parenteral, and topical administration. Preferably, sufficient quantities of the biologically active peptide are delivered to achieve the intended effect. The particular amount of composition to be delivered will depend on many factors, including the effect to be achieved, the type of organism to which the composition is delivered, delivery route, dosage regimen, and the age, health, and sex of the organism. As such, the particular dosage of a composition incorporated into a given formulation is left to the ordinarily skilled artisan's discretion.

Those skilled in the art will appreciate that when the compositions disclosed herein are administered as agents to achieve a particular desired biological result, which may include a therapeutic, diagnostic, or protective effect(s) (including vaccination), it may be possible to combine the minicell composition with a suitable pharmaceutical carrier. The choice of pharmaceutical carrier and the preparation of the minicells as a therapeutic or protective agent will depend on the intended use and mode of administration. Suitable formulations and methods of administration of therapeutic agents include but are not limited to those for oral, pulmonary, nasal, buccal, ocular, dermal, rectal, intravenous, intravesical, intrathecal, intracranial, intratumoral, pleural, or vaginal delivery.

Depending on the mode of delivery employed, the context-dependent functional entity can be delivered in a variety of pharmaceutically acceptable forms. For example, the context-dependent functional entity can be delivered in the form of a solid, suspension, solution, emulsion, dispersion, and the like, incorporated into a pill, capsule, tablet, suppository, aerosol, droplet, or spray. Pills, tablets, suppositories, aerosols, powders, droplets, and sprays may have complex, multilayer structures and have a large range of sizes. Average sizes of aerosols, powders, droplets, and sprays may range from small (submicron) to large (≥200 micron) in size.

Pharmaceutical compositions disclosed herein can be used in the form of a solid, a lyophilized powder, a solution, an emulsion, a dispersion, and the like, wherein the resulting composition contains one or more of the compounds disclosed herein, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The excipients which can be used include glucose, lactose, mannose, gum acacia, gelatin, mannitol, trehalose, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition, auxiliary, stabilizing, thickening, flavoring and coloring agents may be used. Examples of a stabilizing agent include trehalose, preferably at concentrations of 0.1% or greater (See, e.g., U.S. Pat. No. 5,314,695). The active compound is included in the pharmaceutical composition in an amount sufficient to produce the desired effect upon the process or condition of diseases.

6. Terminal Sterilization of Bacterial Minicell Compositions by Ionizing Irradiation Once therapeutic, immunomodulatory, and/or immunogenic minicells are generated, formulated, filled into pharmaceutically acceptable containers, including but not limited to vials or syringes, they are sealed and subjected to terminal sterilization with ionizing irradiation in said container. Non-limiting examples of ionizing irradiation include gamma irradiation, high frequency electromagnetic irradiation, E-beam (electron beam, beta irradiation) irradiation, X-ray (photon) irradiation, and UV irradiation. One of the preferred type of ionizing irradiation for use in the methods and compositions disclosed herein is gamma irradiation.

The dose of ionizing irradiation suitable for use in the methods and compositions disclosed herein can vary. In some embodiments, the dose of ionizing irradiation required for reducing parental cell and adventitious microbial bioburden(s) to acceptable standards of sterility can be empirically determined. Non-limiting exemplary range of the irradiation dose is between 5 kGy and 40 kGy, for example the irradiation can be at a dose of, or at a dose of about, 5 kGy, 8 kGy, 10 kGy, 11 kGy, 12 kGy, 13 kGy, 14 kGy, 15 kGy, 16 kGy, 17 kGy, 18 kGy, 19 kGy, 20 kGy, 21 kGy, 22 kGy, 23 kGy, 24 kGy, 25 kGy, 28 kGy, 30 kGy, 35 kGy, 40 kGy, or a range between any of these values. In some embodiments, the irradiation is at a dose of about 5 kGy to about 30 kGy, or about 10 kGy to about 25 kGy. In some embodiments, the irradiation is at a dose of 25 kGy. The composition comprising minicells suitable for being irradiated for sterilization can be in various forms, including and not limited to, liquid suspension, frozen suspension, and freeze-dried lyophilized (lyophile) cake formulations. In some embodiments, the formulation for sterilization by ionizing irradiation for the composition comprising minicells is a frozen suspension or frozen lyophile. In some embodiments, terminal sterilization of the composition comprising minicells by ionizing irradiation comprises, or is, terminally sterilizing ionizing gamma irradiation at a dose of 25 kGy.

Sterility of a minicell-based biopharmaceutical product can be determined using methods known in the art, for example, as described in USP <71> standards under version USP 38 NF 33. In summary, sterility under USP <71> is defined as no growth (turbidity compared to negative control) in Fluid Thioglycollate Medium (medium sterilized by a validated process) incubated at 32.5° C.±2.5° C. over a 14-day span, post irradiation. Per USP <71>, if the minicell biopharmaceutical product is formulated in liquid of 1 mL or less, and entire vial is used to inoculate growth medium for sterility testing. If over 1 mL but less than 40 mL, half the container but no less than 1 mL is to be used to inoculate sterility test medium. If greater than 40 mL but less than 100 mL, 20 mL shall be used. If over 100 mL, 10% of the container contents, but not less than 20 mL is to be used. If formulated as a solid, including a lyophile, then if less than 50 mg, the entire container contents must be used. If greater than 50 mg and less than 300 mg, then half the mass, but not less than 50 mg is to be used. If greater than 300 mg and less than 5 g, 150 mg is to be used. If greater than 5 g, 500 mg is to be used. The number of containers to be tested in a given production lot under USP <71> include, if less than 100 containers, 10% or 4 containers, whichever is greatest. If greater than 100 containers but fewer than 500, 10 containers are to be used. If more than 500 containers, 2% or 20 containers, whichever is less. For ophthalmic and other non-injectable biopharmaceutical products, if not more than 200 containers, 5% or 2 containers, whichever is greater. If more than 200 containers, 10 containers are required to be tested.

7. Therapeutic Indications and Routes of Administration

The present application relates to minicell-based biopharmaceutical agents designed to be effective against cancer(s), infectious disease(s), genetic disorder(s), autoimmune condition(s), and other maladies.

Cancers include, but are not limited to, solid tumors, metastatic tumors, and liquid tumors. Solid and metastatic tumors include those of epithelial, fibroblast, muscle and bone origin and include but are not limited to breast, lung, pancreatic, prostatic, testicular, ovarian, gastric, intestinal, mouth, tongue, pharynx, hepatic, anal, rectal, colonic, esophageal, urinary bladder, gall bladder, skin, uterine, vaginal, penal, and renal cancers. Other solid cancer types that may be treated with the minicells disclosed herein include but are not limited to adenocarcinomas, sarcomas, fibrosarcomas, and cancers of the eye, brain, and bone. Liquid tumors that can be treated by the minicells disclosed herein include but are not limited to non-Hodgkin's lymphoma, myeloma, Hodgkin's lymphoma, acute lymphocytic leukemia, chronic lymphocytic leukemia, acute myeloid leukemia, chronic myeloid leukemia, and other leukemias.

Infectious disease(s) can be treated prophylactically using immunogenic minicells or targeted minicell vaccine compositions by immunizing a subject prior to its next exposure to the infectious agent against which said vaccine is intended to prevent. Alternatively, a therapeutic vaccine may be given to a subject currently suffering from disease caused by the infectious agent that the vaccine is intended to prevent. Infectious disease(s) include but are not limited to those of bacterial, viral, fungal, and parasitic origin.

Bacterial pathogens against which immunogenic minicells and targeted vaccine minicells are designed to prevent include but are not limited to *Escherichia* spp., *Salmonella* spp., *Shigella* spp., *Vibrio* spp., *Neisseria* spp., *Campylobacter* spp., *Pseudomonas* spp., *Yersinia* spp., *Chlamydia* spp., *Acinetobacter* spp., *Listeria* spp., *Bacillus* spp., *Haemophilus* spp., *Clostridium* spp., *Francisella* spp., *Rickettsia* spp., and others. Immunogenic minicells and targeted minicell vaccines against these agents can be generated from minicells derived from minicell-producing pathogenic strains or from minicells derived from non-pathogenic strains but engineered to recombinantly express or produce a heterologous antigen(s) from a pathogenic strain.

Viral pathogens against which immunogenic minicells and targeted vaccine minicells are designed to prevent include but are not limited to all strains and sub-strains of influenza, parainfluenza, human immunodeficiency virus, Epstein Barr virus, Respiratory Syncitial virus, Varicella zoster, human papilloma virus, hepatitis A virus, hepatitis B virus, hepatitis C virus, dengue fever virus, yellow fever virus, west nile virus, MERS virus, SARS virus, coxsackie virus, herpes simplex virus, cytomegalovirus, rabies virus, and others.

Fungal pathogens against which immunogenic minicells and targeted vaccine minicells are designed to prevent include but are not limited to *Candida* spp., *Aspergillus* spp., *Cryptococcus* spp., *Histoplasma* spp., *Pneumocystis* spp., *Stachybotrys* spp., and others.

Parasitic pathogens against which immunogenic minicells and targeted vaccine minicells are designed to prevent include but are not limited to *Acanthamoeba, Ascaris lumbricoides, Balantidium coli, Cochliomyia hominivorax, Entamoeba histolytica, Fasciola hepatica, Giardia lamblia, Leishmania, Loa loa, Plasmodium falciparum, Schistosoma, Strongyloides stercoralis, Toxoplasma gondii, Trypansoma, Wuchereria bancrofti*, and others.

Minicell-based biopharmaceuticals that have been terminally sterilized by exposure to ionizing irradiation and are intended to treat or otherwise prevent against the disease types and infectious agents listed above may be administered to a subject parenterally or topically. Parenteral routes of administration require injection and include but are not limited to intravenous, intravitreal, intrathecal, intraperitoneal, intratumoral, intramuscular and subcutaneous routes of administration. Topical routes of administration include but are not limited to intravesical, intrarectal, vaginal, mucosal, aural, oral, nasal, pulmonary, intrapleural (through a pleural catheter), and dermal routes of administration.

8. Minicell-Based Pharmaceutical Compositions

Some embodiments disclosed herein relate to creating an optimized strain and preparing targeted therapeutic, immunodulatory, and immunogenic minicells from, but not limited to, the bacterial family Enterobacteriaceae; formulating said minicells into a pharmaceutical composition; filling into sterile vials or syringes; sealing, and terminally sterilizing the minicell-based pharmaceutical composition by exposure to ionizing irradiation.

Also disclosed herein is a pharmaceutical composition comprising a plurality of bacterial minicells, wherein the bacterial minicells and/or the pharmaceutical composition have been exposed to ionizing irradiation. The pharmaceutical composition can, for example, comprise one or more pharmaceutically acceptable excipient or a pharmaceutically acceptable diluent. The pharmaceutically acceptable excipient can be, for example, trehalose (e.g., trehalose in diluent). The pharmaceutically acceptable diluent can be, for example, sterile water (e.g., sterile water for injection). In some embodiments, the pharmaceutical composition and/or the plurality of bacterial cells contained therein have been terminally sterilized. In some embodiments, the pharmaceutical composition is sterile. For example, the pharmaceutical composition can contain viable microbial contaminants at a level conforming to USP <71> standards under version USP 38 NF 33. The level of viable microbial contaminants in the pharmaceutical composition that has been exposed to ionizing irradiation (e.g., gamma irradiation) can be, for example, less than $1 \times 10^8$ colony forming units (CFU) per mL, less than $1 \times 10^7$ CFU per mL, less than $1 \times 10^6$ CFU per mL, less than $1 \times 10^5$ CFU per mL, less than $1 \times 10^4$ CFU per mL, less than $1 \times 10^3$ CFU per mL, less than $1 \times 10^2$ CFU per mL, less than 10 CFU per mL, or less than 1 CFU per mL. In some embodiments, the level of viable microbial contaminants in the pharmaceutical composition that has been exposed to ionizing irradiation (e.g., gamma irradiation) can be, or can be about, $1 \times 10^8$ CFU per mL, $5 \times 10^7$ CFU per mL, $1 \times 10^7$ CFU per mL, $5 \times 10^6$ CFU per mL, $1 \times 10^6$ CFU per mL, $5 \times 10^5$ CFU per mL, $1 \times 10^5$ CFU per mL, $5 \times 10^4$ CFU per mL, $1 \times 10^4$ CFU per mL, $5 \times 10^3$ CFU per mL, $1 \times 10^3$ CFU per mL, $5 \times 10^2$ CFU per mL, $1 \times 10^2$ CFU per mL, 50 CFU per mL, 10 CFU per mL, 5 CFU per mL, 1 CFU per mL, or a range between any two of these values.

The level of minicell-producing viable microbial contaminants contamination in the pharmaceutical composition following exposure to ionizing irradiation can be, for example, less than 1 in $10^2$ minicells, less than 1 in $10^3$ minicells, less than 1 in $10^4$ minicells, less than 1 in $10^5$ minicells, less than 1 in $10^6$ minicells, less than 1 in $10^7$ minicells, less than 1 in $10^8$ minicells, less than 1 in $10^9$ minicells, less than 1 in $10^{10}$ minicells, less than 1 in $10^{11}$ minicells, less than 1 in $10^{12}$ minicells, less than 1 in $10^{13}$ minicells, less than 1 in $10^{14}$ minicells, less than 1 in $10^{15}$ minicells, or less than 1 in $10^{16}$ minicells.

The types, genotypes and phenotypes of the minicells comprised in the pharmaceutical can vary. In some embodiments, said bacterial minicells express and/or display invasin or a functional equivalent thereof on their surfaces. For example, the invasin can be, but is not limited to, an invasin from *Yersinia pseudotuberculosis*. The bacterial minicells can, for example, comprise perfringolysin O (PFO). In some embodiments, the bacterial minicells express and/or displays invasin or a functional equivalent thereof on their surfaces, and comprise PFO.

In some embodiments, the level of minicell-producing viable parental cell contamination in the pharmaceutical composition following exposure to ionizing irradiation is less than 1 in $10^5$ minicells.

In some embodiments, the level of minicell producing viable parental cell contamination in the pharmaceutical composition following exposure to ionizing irradiation is less than 1 in $10^6$ minicells.

In some embodiments, the level of minicell producing viable parental cell contamination in the pharmaceutical composition following exposure to ionizing irradiation is less than 1 in $10^7$ minicells.

In some embodiments, the level of minicell producing viable parental cell contamination in the pharmaceutical composition following exposure to ionizing irradiation is less than 1 in $10^8$ minicells.

In some embodiments, the level of minicell producing viable parental cell contamination in the pharmaceutical composition following exposure to ionizing irradiation is less than 1 in $10^9$ minicells.

In some embodiments, the level of minicell producing viable parental cell contamination in the pharmaceutical composition following exposure to ionizing irradiation is less than 1 in $10^{10}$ minicells.

In a preferred embodiment, the level of minicell producing viable parental cell contamination in the pharmaceutical composition following exposure to ionizing irradiation is less than 1 in $10^{11}$ minicells.

In some embodiments, the level of minicell producing viable parental cell contamination in the pharmaceutical composition following exposure to ionizing irradiation is less than 1 in $10^{12}$ minicells.

In some embodiments, the level of minicell producing viable parental cell contamination in the pharmaceutical composition following exposure to ionizing irradiation is less than 1 in $10^{13}$ minicells.

In some embodiments, the level of minicell producing viable parental cell contamination in the pharmaceutical composition following exposure to ionizing irradiation is less than 1 in $10^{14}$ minicells.

In some embodiments, the level of minicell producing viable parental cell contamination in the pharmaceutical composition following exposure to ionizing irradiation is less than 1 in $10^{15}$ minicells.

In some embodiments, the level of minicell producing viable parental cell contamination in the pharmaceutical composition following exposure to ionizing irradiation is less than 1 in $10^{16}$ minicells.

Following exposure to ionizing irradiation, the pharmaceutical composition comprising the minicells (e.g., a minicell-based biopharmaceutical product) is devoid of growth in Liquid Thioglycollate Medium after, or after about, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, or a range between any two of these values, at, for example, 32.5° C.±2.5° C. In one of the preferred embodiments, following exposure to ionizing irradiation, a minicell-based biopharmaceutical product is devoid of growth in Liquid Thioglycollate Medium after 14 days at 32.5° C.±2.5° C. and therefore is sterile as per the definition of USP <71> standards under version USP 38 NF 33.

EXAMPLES

Some aspects of the embodiments discussed above are disclosed in further detail in the following examples, which are not in any way intended to limit the scope of the present disclosure.

Example 1

No Change in VAX-IP (VAX014) Minicell Properties in a Frozen Suspension Following Exposure to Ionizing Gamma Irradiation at Doses of 5, 15 and 25 kGy

This example shows that there was no change in VAX-IP (VAX014) minicell properties following exposure to ionizing gamma irradiation in a frozen suspension at doses of 5, 15 and 25 kGy.

VAX014 minicells (contains both Invasin and Perfringolysin O) were made from parental strain VAX20B9, a recombinant *Escherichia coli* K-12 minicell-producing strain harboring the L-rhamnose-inducible bacterial expression plasmid, pVX-336 (containing a transcriptional fusion between Invasin and Perfringolysin O under control of the pRHA$_{BAD}$ promoter). One vial of VAX20B9 research cell bank was thawed at room temperature and the entire vial contents used to inoculate a 1 L starter culture in Soytone-based MSB-NaCl media containing kanamycin (50 µg/mL), diaminopimelic acid (100 µg/mL), lysine (55 µg/mL), and 0.2% D-glucose. The starter culture was grown for 18 hours at 30° C. and the following day, 200 mL used to inoculate 14 L of identical media, without D-glucose. Growth was monitored until an OD$_{600}$ of 0.1 was reached, at which time L-rhamnose was added to induce for the expression of Invasin and Perfringolysin O from pVX-336. Growth was then monitored until an OD$_{600}$ of 1.0 was reached, at which time IPTG was added to a final concentration of 20 µM to induce for the minicell-production phenotype and culture allowed to grow overnight. Culture was de-bulked of parental cells by differential centrifugation (15 min at 2,000×g) and minicell-enriched supernatant concentrated by tangential flow filtration (TFF) prior to further purification using two sequential linear density sucrose gradients. The final minicell fractions were concentrated by (TFF), then pelleted by high-speed centrifugation (20 min at 11,000×g) and the final VAX014 minicell pellets resuspended in 12% sterile D-trehalose in pharmaceutical grade water at a concentration of 3.33×10$^{10}$ VAX014 minicells per milliliter to make bulk drug substance. Once at the target concentration, 100 µL of bulk drug substance was plated on Soytone-based MSB-NaCl solid agar medium containing diaminopimelic acid (100 µg/mL) and lysine (55 µg/mL) and allowed to grow overnight at 30° C. to determine the number of contaminating VAX20B9 parental cells and any additional adventitious microbe(s) prior to sterilization by gamma irradiation. Bulk VAX014 drug substance was then vialed (3 mL per vial—1×10$^{11}$ VAX014 minicells per vial) into 5 mL clear serum vials using a semi-automated hand-fill, and each vial stoppered and sealed. Vialed VAX014 drug substance was then exposed to one of three irradiation doses (5, 15, or 25 kGy, 25 vials irradiated at each dose level) while frozen. On Day 7 post-irradiation, 3 randomly selected vials were thawed at room temperature and VAX014 drug product characterized using a battery of characterization tests including concentration uniformity, appearance, container closure integrity, visual inspection, pH testing, microscopic evaluation of product aggregation and presence of particulate matter, determination of the amount of Invasin on the VAX014 minicell surface by FACS using a monoclonal antibody against Invasin, the hemolytic activity of Perfringolysin O on whole citrated sheep blood, cell killing potency of VAX014 against HTB-9 human urothelial carcinoma cells, and the final viable colony forming unit counts as a measure of the reduction in bioburden from non-irradiated material.

The experimental results are summarized in Table 2. As shown in Table 2, no changes in product integrity, stability, characteristics, and potency were observed for a frozen suspension of VAX014 minicells after being exposed to ionizing gamma irradiation at doses of 5 kGy, 15 kGy and 25 kGy as compared to non-irradiated material. The bioburden was reduced to zero at each dose level.

TABLE 2

Properties of compositions comprising minicells before and after gamma irradiation
FORMULATION: Frozen Suspension VAX014 (1 × 10$^{11}$) in 3 mL 12% sterile D-Trehalose

| PROPERTY | DOSE | | | |
|---|---|---|---|---|
| | 0 | 5 kGy | 15 kGy | 25 kGy |
| Glass Color (VI) | Clear | Brown | Slightly Darker Brown | Much Darker Brown |
| Stopper intact (VI) | Y | Y | Y | Y |
| Seal intact (VI) | Y | Y | Y | Y |
| Change in DS appearance (VI) | N | N | N | N |
| Precipitates (MI) | N | N | N | N |
| Aggregates (MI) | <5% | <5% | <5% | <5% |
| OD600 | 1.86 | 2.06 | 1.99 | 2.02 |
| FACS against Invasin (% positive) | 83.6 | 86.9 | 88.9 | 89.4 |
| PFO hemolytic activity (PFO ng/10$^8$ mcs) | 34.6 | 32.6 | 36.1 | 40.6 |
| Potency (cell killing - immediate) (VAX-IP::HTB-9 ratio @ IC50) | 41.31 | 46.16 | 47.21 | 49.27 |
| Potency (cell killing - 4 hour at room temperature before testing) (VAX-IP::HTB-9 ratio @ IC50) | 42.3 | 48.3 | 43.0 | 47.9 |
| CFU (VAX20B9) (CFU/10$^{10}$ mcs) | 5098 | 0 | 0 | 0 |
| pH | 5.54 | 5.20 | 5.53 | 5.45 |

VI = Visual Inspection,
MI = Microscopic Inspection

Example 2

No Change in VAX-IP (VAX014) Minicell Properties in a Frozen Lyophile Following Exposure to Ionizing Gamma Irradiation at Doses of 5, 15 and 25 kGy

This example shows that there was no change in VAX-IP (VAX014) minicell properties following exposure to ionizing gamma irradiation in a frozen lyophile at doses of 5, 15 and 25 kGy.

VAX014 minicells (contains both Invasin and Perfringolysin O) are made from parental strain VAX20B9, a recombinant *Escherichia coli* K-12 minicell-producing strain harboring the L-rhamnose-inducible bacterial expression plasmid, pVX-336 (contains a transcriptional fusion between Invasin and Perfringolysin O under control of the pRHA$_{BAD}$ promoter). One vial of VAX20B9 research cell bank was thawed at room temperature and the entire vial contents used to inoculate a 1 L starter culture in Soytone-based MSB-NaCl media containing kanamycin (50 µg/mL), diaminopimelic acid (100 µg/mL), lysine (55 µg/mL), and 0.2% D-glucose. The starter culture was grown for 18 hr at 30° C. and the following day, 200 mL used to inoculate 14 L of identical media, without D-glucose. Growth was monitored until an OD$_{600}$ of 0.1 was reached, at which time L-rhamnose was added to induce for the expression of Invasin and Perfringolysin O from pVX-336. Continued growth was then monitored until an OD$_{600}$ of 1.0 was reached, at which time IPTG was added to a final concentration of 20 µM to induce for the minicell-production phenotype and culture allowed to grow overnight. Culture was de-bulked of parental cells by differential centrifugation (15 min at 2,000×g) and minicell-enriched supernatant concentrated by tangential flow filtration (TFF) prior to further purification using two sequential linear density sucrose gradients. The final minicell fractions were concentrated by (TFF), then pelleted by high-speed centrifugation (20 min at 11,000×g) and the final VAX014 minicell pellets resuspended in 12% sterile D-trehalose in pharmaceutical grade water at a concentration of 3.33×10$^{10}$ VAX014 minicells per milliliter to make bulk drug substance. Once at the target concentration, 100 µL of bulk drug substance was plated on Soytone-based MSB-NaCl solid agar medium containing diaminopimelic acid (100 µg/mL) and lysine (55 µg/mL) and allowed to grow overnight at 30° C. to determine the number of contaminating VAX20B9 parental cells and any additional adventitious microbe(s) prior to sterilization by gamma irradiation. Bulk VAX014 drug substance was then vialed (3 mL per vial—1×10$^{11}$ VAX014 minicells per vial) into 5 mL clear serum vials using a semi-automated hand-fill, and each vial stoppered with a NovaPure lyophilization compatible stopper. Vial contents were lyophilized and then overseals applied. Vialed, lyophilized VAX014 drug substance was then exposed to one of three irradiation doses (5, 15, or 25 kGy, 25 vials irradiated at each dose level) while frozen. On Day 7 post-irradiation, 3 randomly selected vials were thawed at room temperature and VAX014 drug product characterized using a battery of characterization tests including concentration uniformity, appearance, container closure integrity, visual inspection, pH testing, microscopic evaluation of product aggregation and presence of particulate matter, determination of the amount of Invasin on the VAX014 minicell surface by FACS using a monoclonal antibody against Invasin, the hemolytic activity of Perfringolysin O on whole citrated sheep blood, cell killing potency of VAX014 against HTB-9 human urothelial carcinoma cells, and the final viable colony forming unit counts as a measure of the reduction in bioburden from non-irradiated material. No changes in product integrity, stability, characteristics, and potency were observed, while the bioburden was reduced to zero at each dose level.

The experimental results are summarized in Table 3. As shown in Table 3, there was no change in the properties and characteristics of a frozen lyophilized VAX014 minicells after exposure to ionizing gamma irradiation at doses of 5 kGy, 15 kGy and 25 kGy as compared to non-irradiated material.

TABLE 3

Properties of compositions comprising minicells before and after gamma irradiation
FORMULATION: Frozen Lyophile VAX014 (1 × 10$^{11}$) lyophilized from 3 mL 12% sterile D-Trehalose

| | DOSE | | | |
|---|---|---|---|---|
| PROPERTY | 0 | 5 kGy | 15 kGy | 25 kGy |
| Glass Color (VI) | Clear | Brown | Slightly Darker Brown | Much Darker Brown |
| Stopper intact (VI) | Y | Y | Y | Y |
| Seal intact (VI) | Y | Y | Y | Y |
| Change in DS appearance (VI) | N | N | N | N |
| Precipitates (MI) | N | N | N | N |
| Aggregates (MI) | <5% | <5% | <5% | <5% |
| OD600 | 1.60 | 1.62 | 1.73 | 1.71 |
| FACS against Invasin (% positive) | 86.7 | 83.6 | 89.5 | 88.9 |
| PFO hemolytic activity (PFO ng/10$^8$ mcs) | 34.9 | 29.4 | 28.8 | 37.9 |
| Potency (cell killing - immediate) (VAX-IP::HTB-9 ratio @ IC50) | 50.87 | 56.55 | 49.7 | 51.56 |
| Potency (cell killing - 4 hr at room temperature before testing) (VAX-IP::HTB-9 ratio @ IC50) | 51.9 | 54.4 | 41.4 | 47.2 |
| CFU (VAX20B9) (CFU/10$^{10}$ mcs) | 250 | 0 | 0 | 0 |
| pH | 5.52 | 5.05 | 4.94 | 5.77 |

VI = Visual Inspection,
MI = Microscopic Inspection

Example 3

Figure 2A:
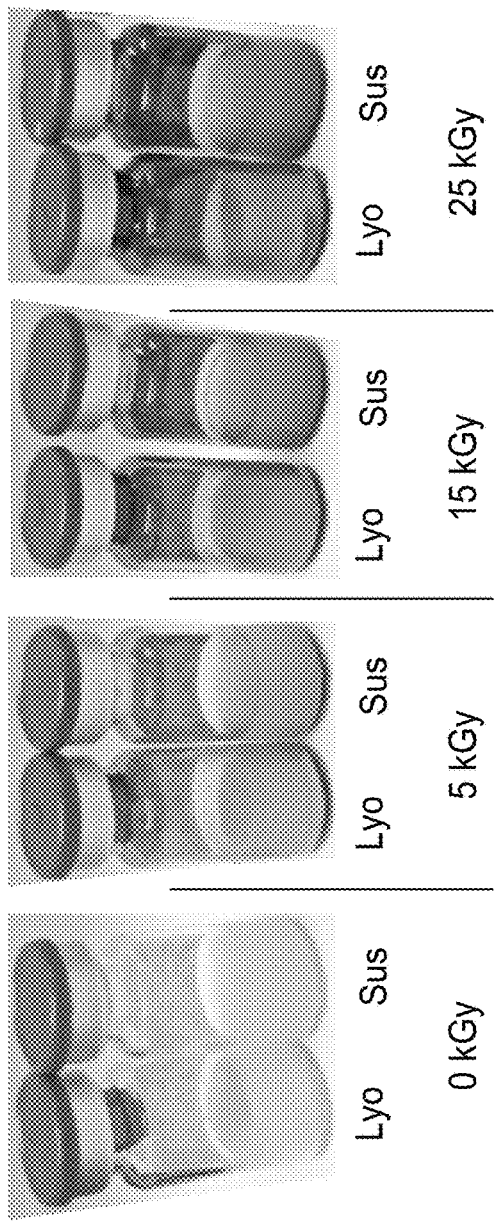
FIGS. 2A-B show VAX014 minicell containing vials (frozen suspension or frozen lyophile) that have been exposed to increasing doses of gamma irradiation.
Figure 2B:
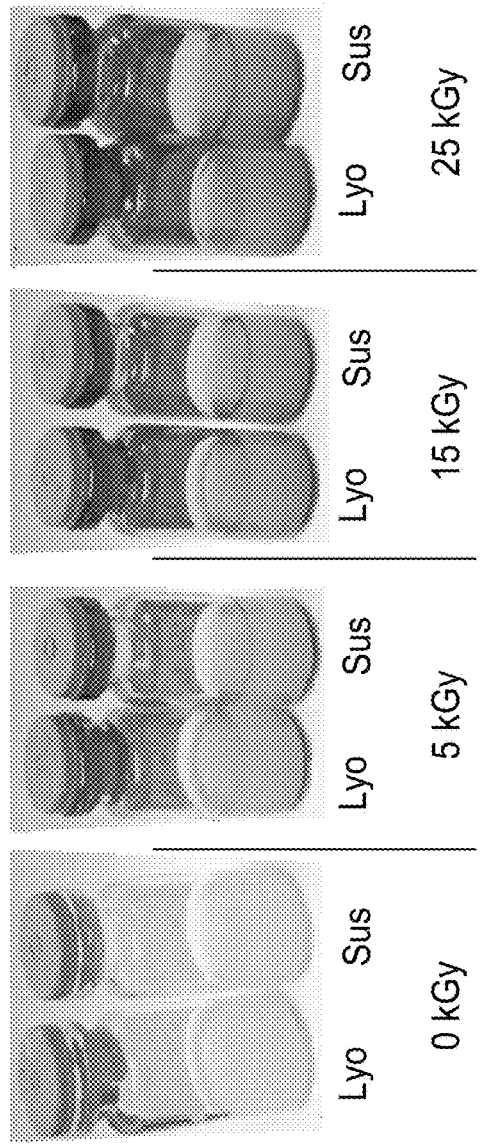

Studies of Minicell-Containing Compositions Following Exposure to Gamma Irradiation Clear vials were selected for the purpose of ensuring and demonstrating that increasing levels of ionizing gamma irradiation were administered. Vials containing minicells were exposed to gamma irradiation at 5 kGy, 15 kGy or 25 kGy, and compared to non-irradiated controls (i.e., 0 kGy). FIGS. 2A-B show the results of the initial visual inspection, held at the vial level, post-irradiation. It was found that vials were darkened with increasing irradiation dose level, yet there was no visual loss of product (including volume and drug substance). FIG. 2A shows sealed vials and FIG. 2B shows vials where the seals have been removed and the stoppers remain intact upon visual inspection. No macroscopic abnormalities were observed in the over-seal or stopper.

Figure 3:
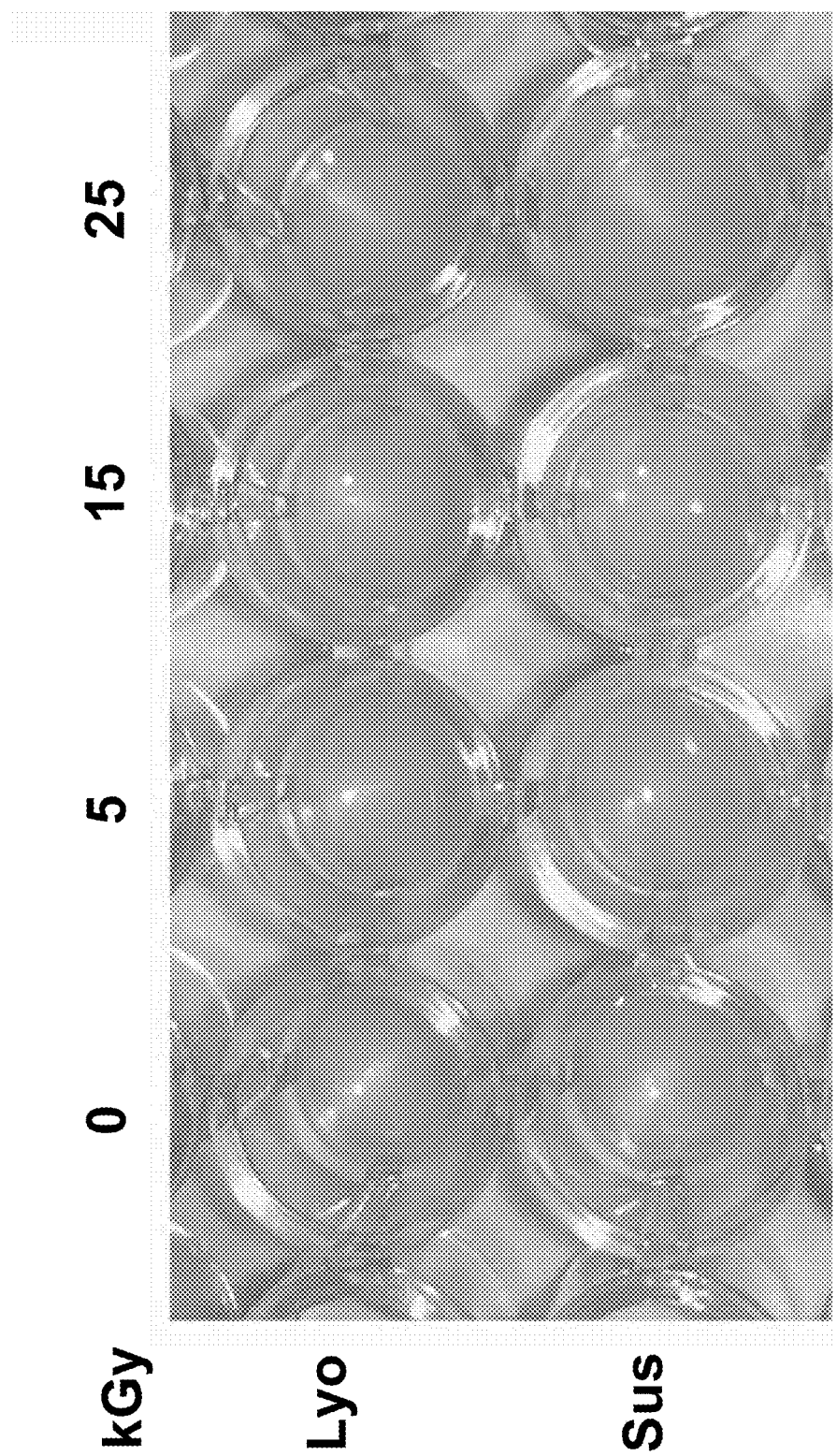
FIG. 3 shows reconstituted lyophilized VAX014 minicells and thawed frozen suspension of VAX014 minicells that have been exposed to increasing doses of gamma irradiation after removal from the container for visual inspection.

FIG. 3 further shows that there was no change in appearance (including color, consistency, and opaqueness) per secondary visual inspection of irradiated VAX014 drug product when removed from vials as compared to non-irradiated controls. Lyophiles were reconstituted in 3 mL of sterile water for injection prior to visual inspection.

Figure 4:
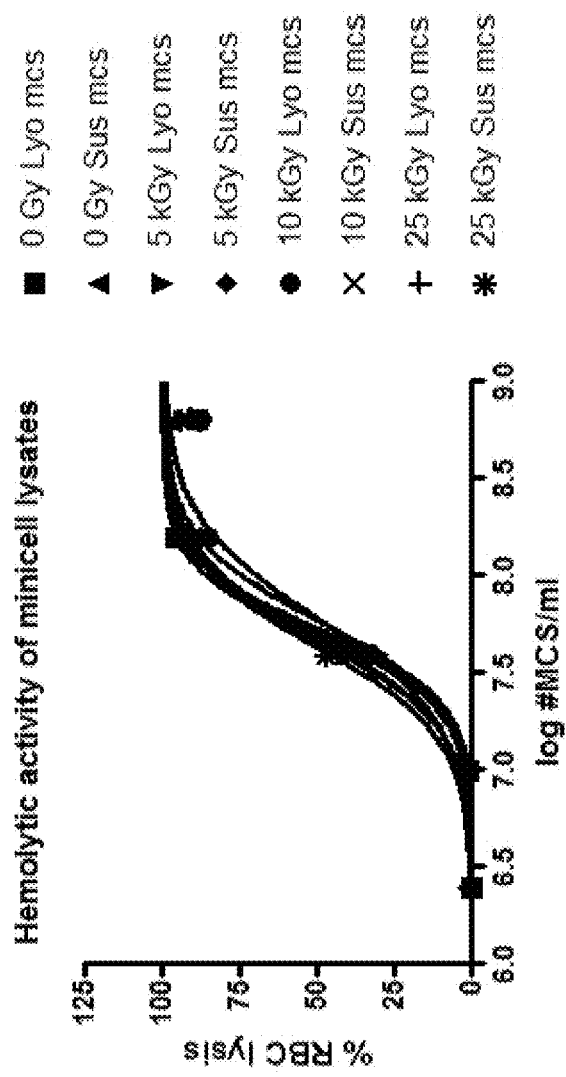
FIG. 4 shows hemolytic activity (i.e., perfringolysin O activity) in VAX014 minicell frozen suspension and frozen lyophiles after being exposed to increasing amounts of ionizing gamma irradiation.

Hemolytic activities of the minicell-containing compositions after being exposed to gamma irradiation were studied. As shown in FIG. 4, the structure-function of Perfringolysin O protein toxin in VAX014 minicell lysates was not affected by gamma irradiation at any level tested (including 5 kGy, 10 kGy and 25 kGy) as compared to the non-irradiated control. In this study, irradiated and non-irradiated minicells were treated with EDTA and lysozyme, followed by osmotic shock to generate whole minicell lysates, each of which was then titrated against a fixed number of sheep red blood cells for 1 hour at 37° C. while shaking. Following a 1 hour co-incubation, red blood cells (RBCs) were pelleted and the supernatants removed and evaluated for hemoglobin release as a measure of hemolytic activity. A standard curve using recombinant PFO was generated in parallel and used to calculate the concentration of Perfringolysin O in $1 \times 10^8$ VAX014 minicells. Therefore, there was no loss of perfringolysin O (protein toxin) activity in VAX014 minicell frozen suspension or frozen lyophiles after exposure to increasing amounts of ionizing gamma irradiation.

Figure 5A:
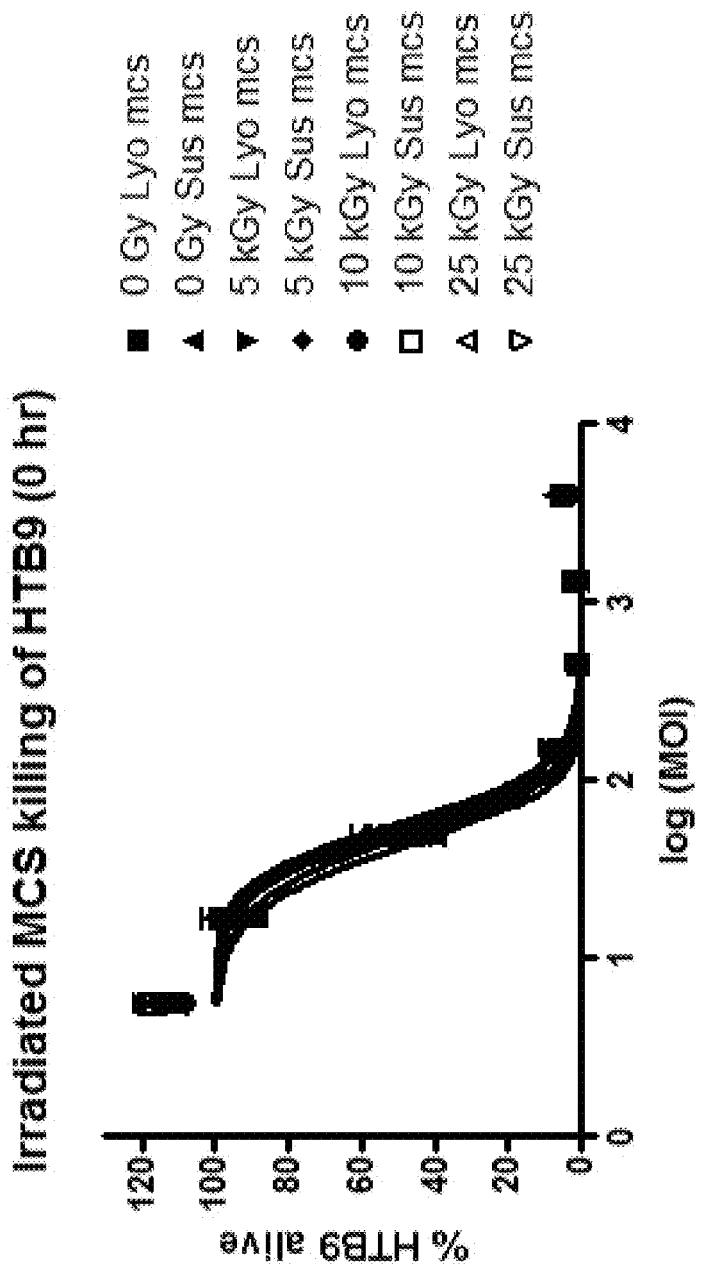
FIGS. 5A-B are plots of VAX014 minicell-mediated cell-killing activity (potency) of VAX014 minicell frozen suspension or frozen lyophiles after being exposed to increasing amounts of ionizing gamma irradiation.
Figure 5B:
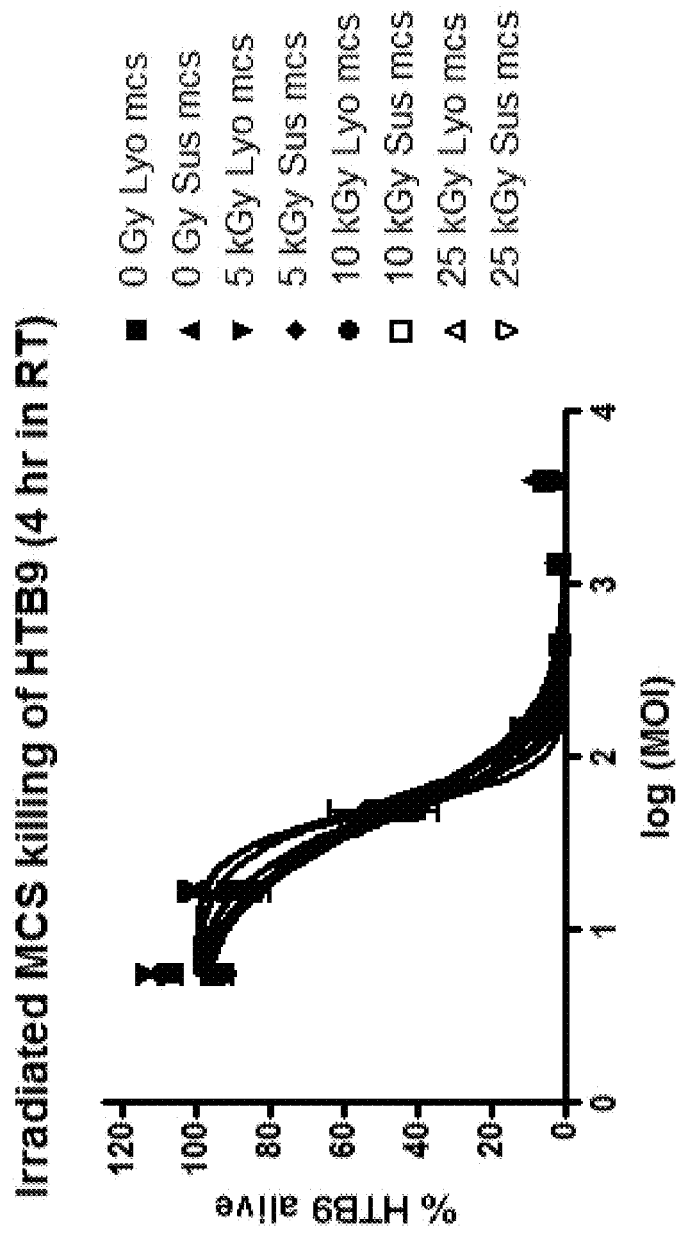
Figure 6:
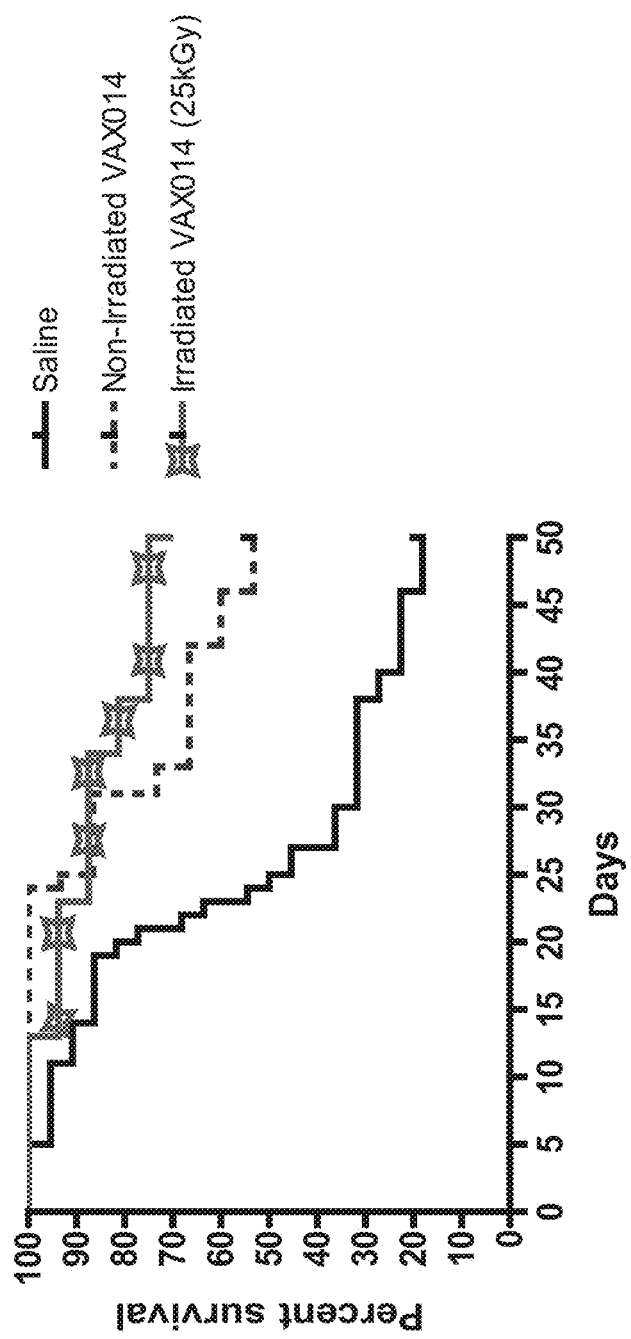
FIG. 6 is a Kaplan-Meier survival curve demonstrating no loss in VAX014 anti-tumor activity following sterilization at 25 kGy in the MB49 syngeneic orthotopic murine model of bladder cancer after intravesical administration to tumor bearing mice as compared to pre-sterilized non-irradiated VAX014.
Figure 7A:
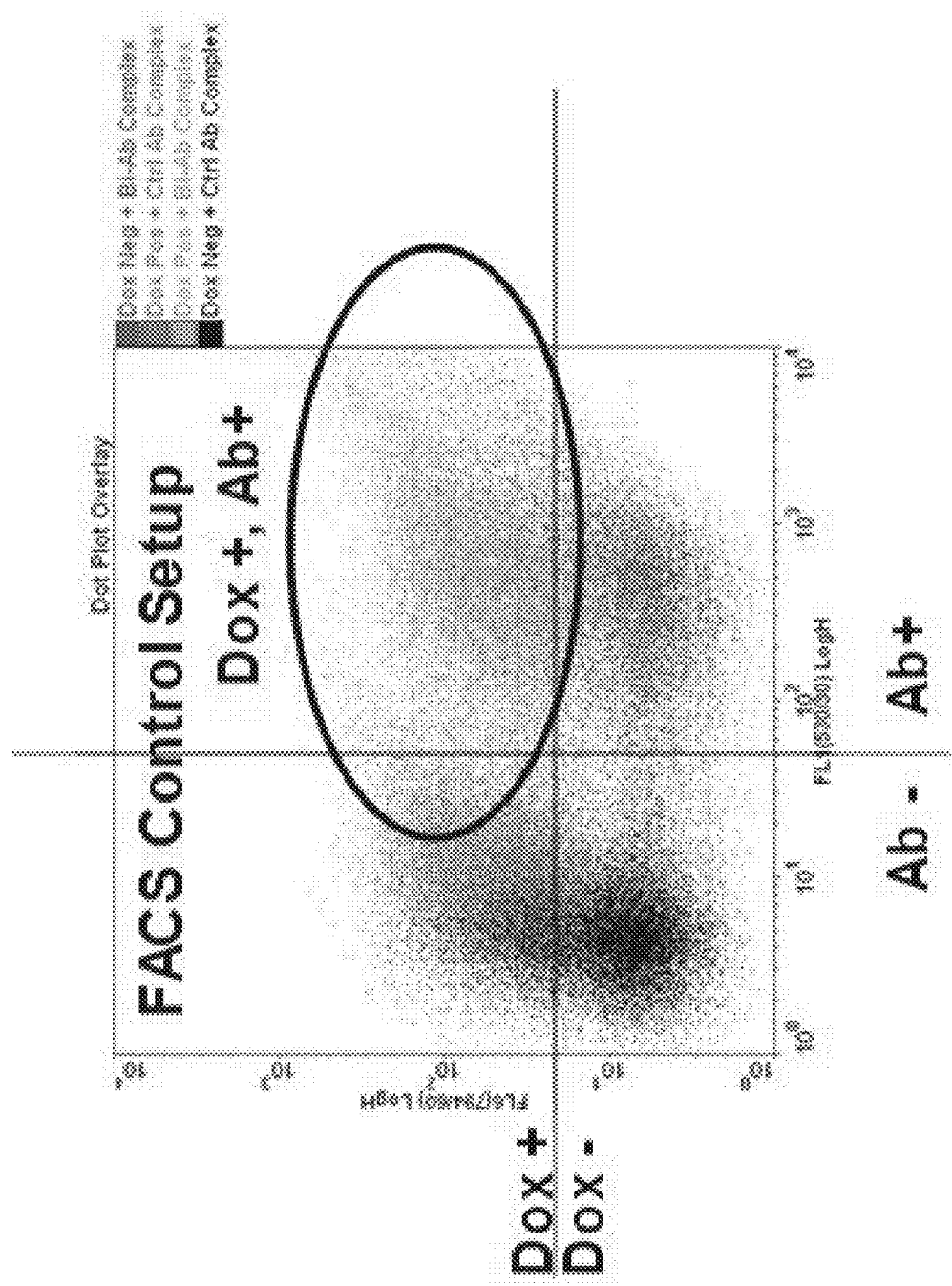
FIGS. 7A-F show no loss of stability, integrity, or potency of minicells after gamma irradiation at 25 kGy, where the minicells comprise doxorubicin and display an antibody against human Epidermal Growth Factor Receptor 1 (EGFR-1) on their surfaces.
Figure 7B:
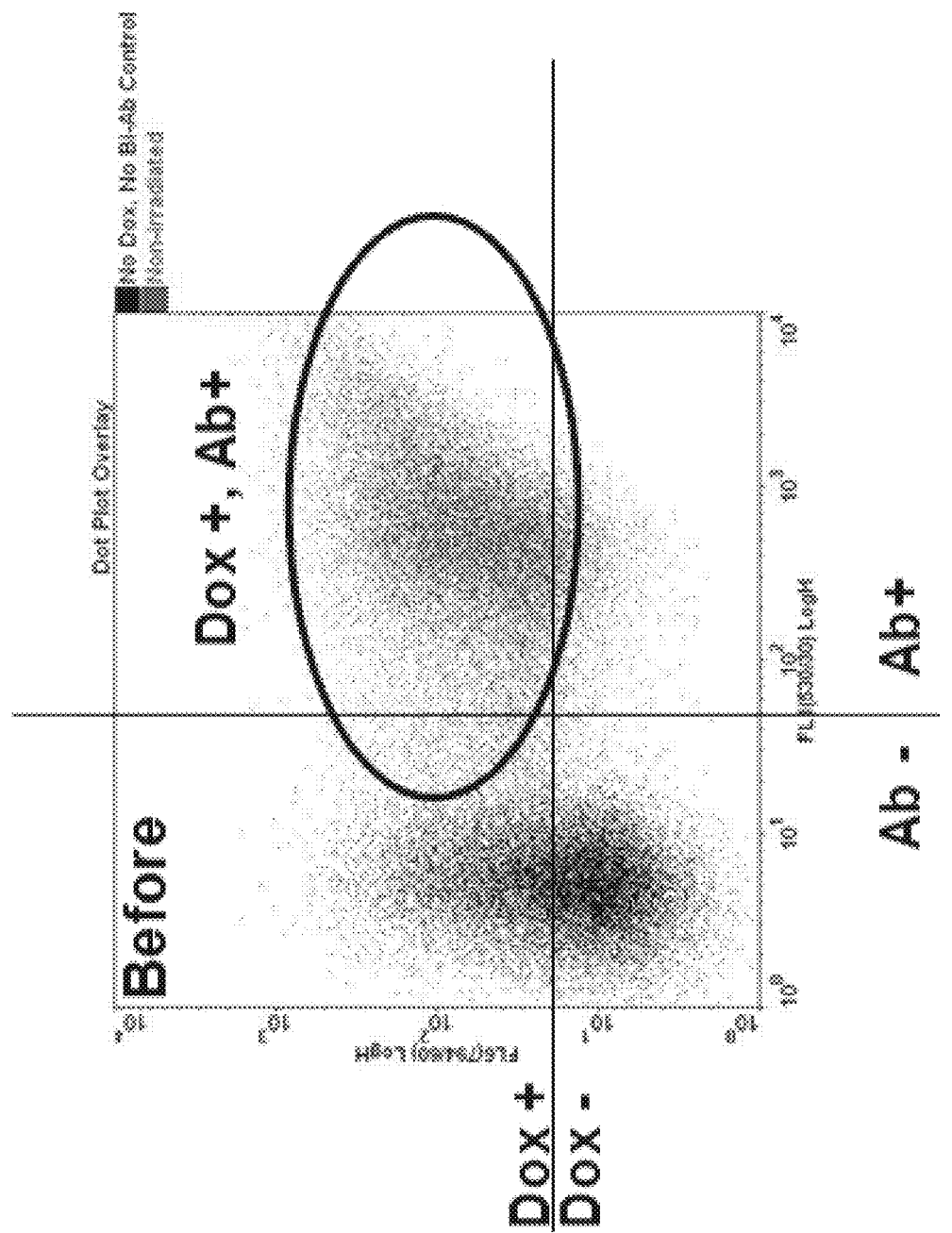
Figure 7C:
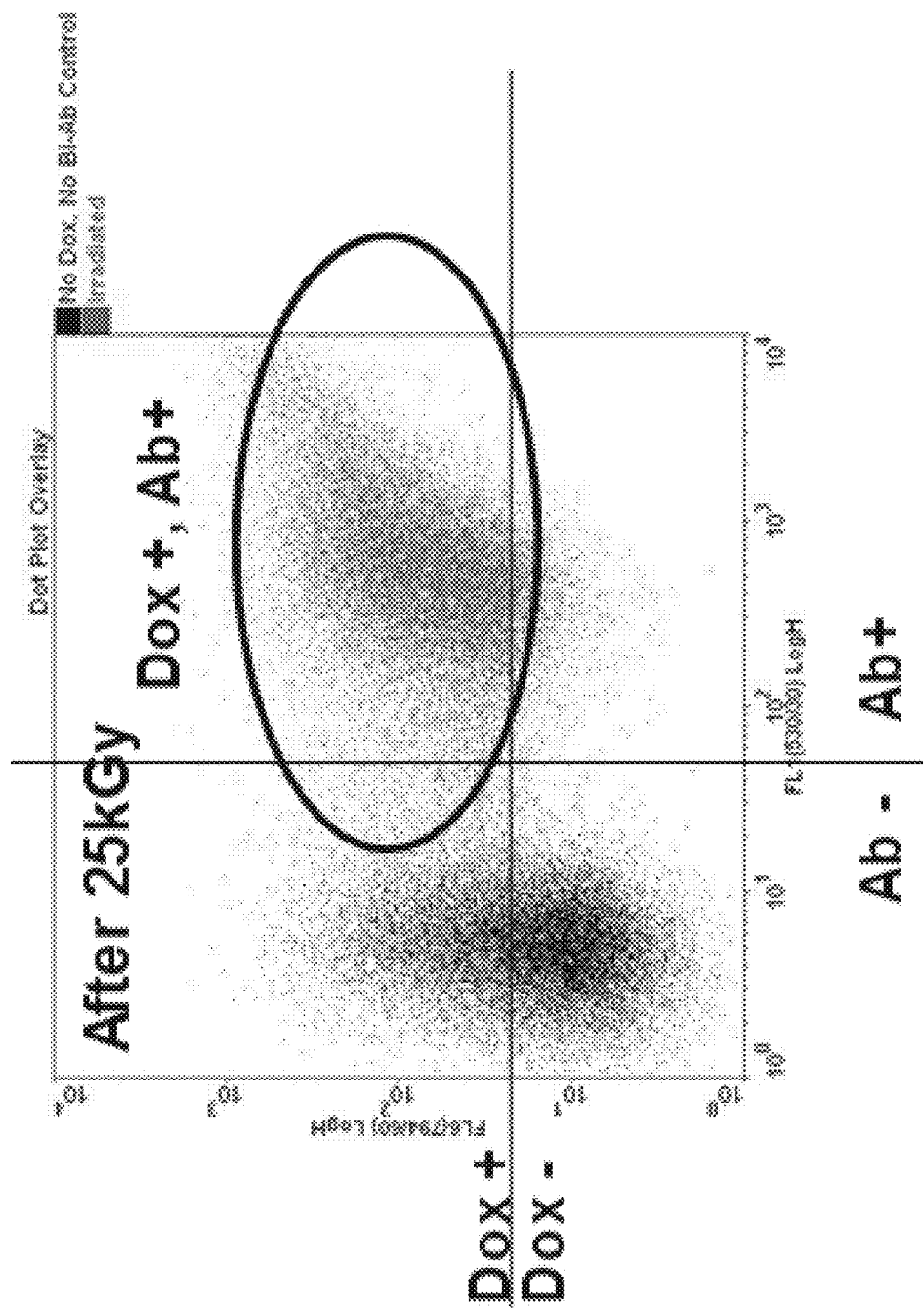
Figure 7D:
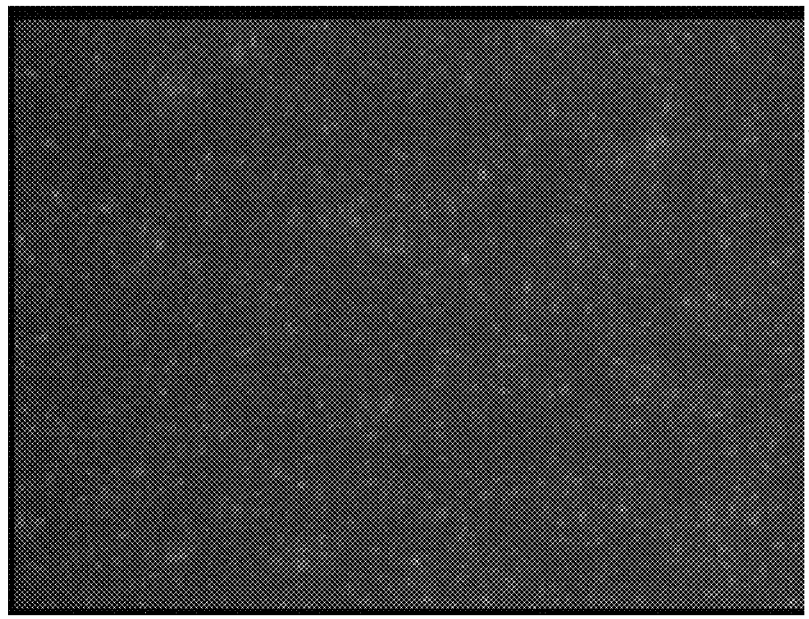
Figure 7D:
Figure 7E:
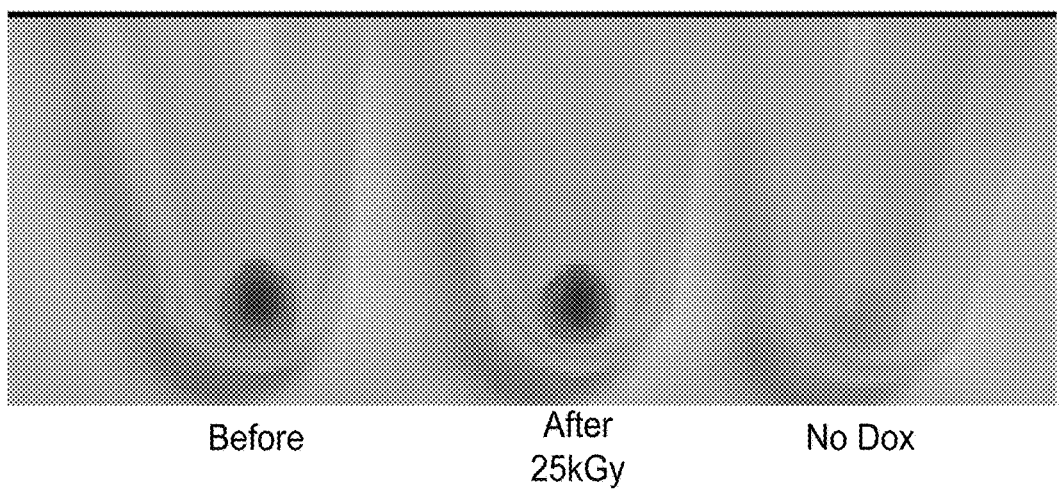
Figure 7F:
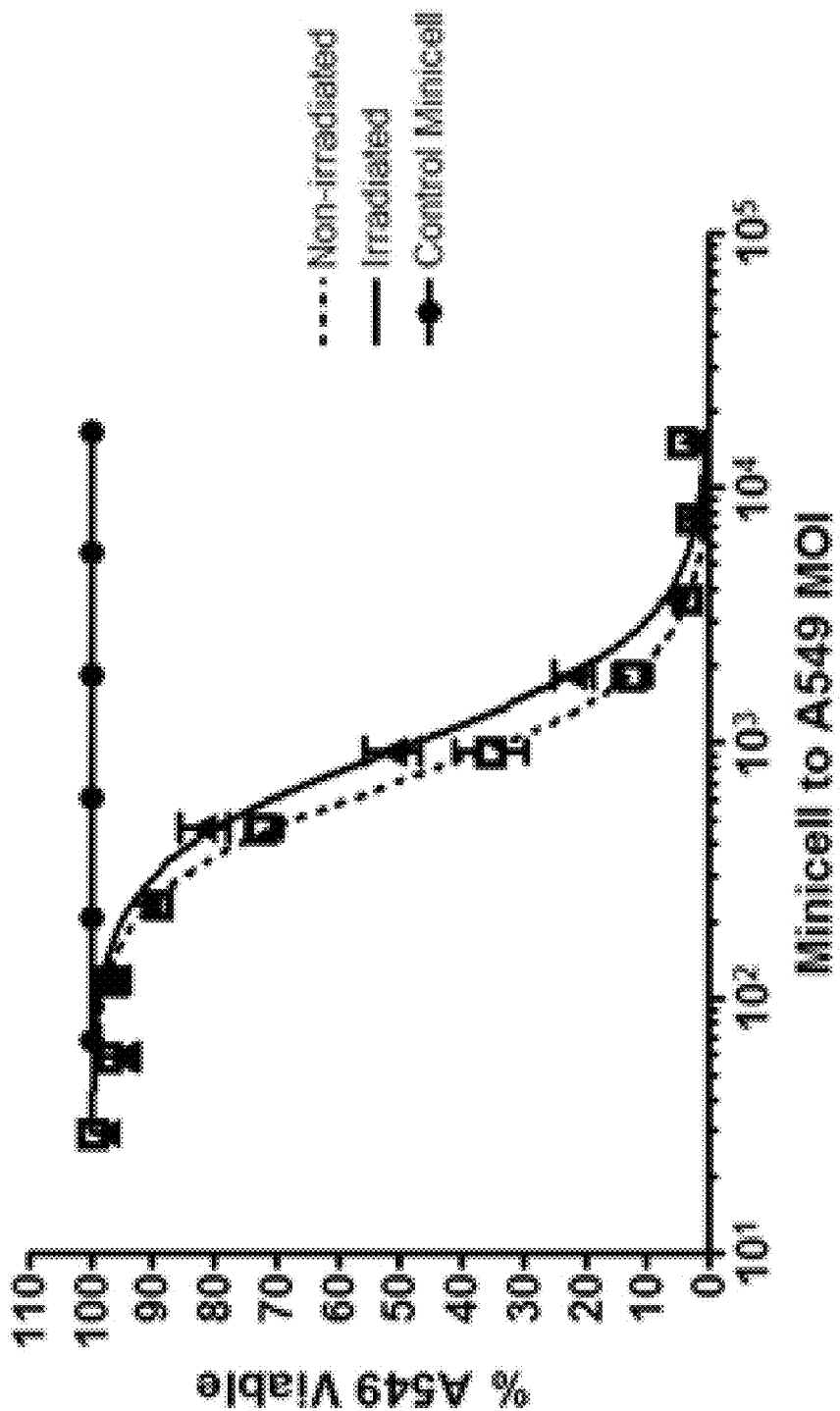

Potency of the minicells following gamma irradiation (at 5 kGy, 10 kGy or 25 kGy) was also evaluated using a cell-killing potency assay against HTB-9 human urothelial carcinoma cells as compared to non-irradiated controls. Vials of irradiated and non-irradiated VAX014 minicells were thawed at room temperature and immediately titrated against a fixed number of HTB-9 cells to generate $EC_{50}$ curves (0 hour, FIG. 5A). In addition, thawed vials were allowed to remain at room temperature for 4 hr prior to addition to HTB-9 cells to demonstrate no loss of activity over this time frame at this temperature (4 hour in room temperature (RT), FIG. 5B). As shown in FIGS. 5A-B, all $EC_{50}$ values overlap, demonstrating no loss in potency of VAX014 minicell frozen suspension or frozen lyophiles after being exposed to increasing amount of gamma irradiation.

Pharmacological activity of the minicells following gamma irradiation (at 5 kGy, 10 kGy or 25 kGy) was also studied in vivo using the murine syngeneic orthotopic MB49 bladder cancer model compared to non-irradiated controls. In these experiments, 100,000 MB49 cells were instilled in a 50 µL volume of DMEM cell culture medium directly into the bladders of anesthetized female C57BL/6 mice (n=8 per group) via urinary catheter. Prior to instillation, bladders were cauterized at two sites using a platinum guidewire attached to a Bovie electrocautery unit and a 2 second monopolar pulse at 5 W applied at two separate intra-bladder contact points (provides tumor attachment sites). Following tumor cell installation, bladders were rinsed once with 100 µL of sterile saline and then saline (vehicle control) or an equivalent number of either irradiated (25 kGy) or non-irradiated VAX014 minicells administered in a 50 µL volume as a single dose treatment. Catheters were locked for a total 1 hour treatment exposure time, then removed, and animals allowed to recover. Animals were monitored twice weekly for 70 days and comparative survival curves evaluated as a measure of pharmacological efficacy. The results are summarized in FIG. 9 demonstrates no loss of VAX014 pharmacological activity in vivo The results are summarized in a Kaplan-Meier survival curve shown in FIG. 9. As shown in FIG. 9, there was no loss in VAX014 anti-tumor activity following sterilization at 25 kGy in the MB49 syngeneic orthotopic murine model of bladder cancer after intravesical administration to tumor bearing mice as compared to pre-sterilized non-irradiated VAX014.

Integrity, stability, and activity of EGFR-1 targeted minicells containing doxorubicin were also evaluated for their response to increasing levels of gamma irradiation. Minicells generated from an *Escherichia coli* K-12 strain (strain VAX8I3) with an inducible minicell phenotype were generated by growing this strain on Soytone-based MSB-NaCl media containing diaminopimelic acid (100 µg/mL) and lysine (55 µg/mL) at 30° C. until an $OD_{600}$ of 1.0 was reached. At that point, IPTG was added to induce for the minicell production phenotype and the culture allowed to continue growing overnight. Minicells were harvested using differential centrifugation followed by two sequential rounds of linear density sucrose gradients. Following purification, minicells ($3 \times 10^{12}$) were loaded with doxorubicin by co-incubation with doxorubicin at a concentration of 400 µg/mL/$1.0 \times 10^{10}$ minicells overnight at room temperature while shaking. The following day, bi-specific antibodies were generated by coupling human EGFR-1-specific mouse monoclonal antibody mAb528 to a Protein A-purified polyclonal rabbit anti-minicell antibody reagent at a molar ratio of 1:1 using recombinant Protein A/G (Pierce, Thermo-Fisher). Antibodies were mixed in equimolar amount prior to addition of Protein A/G. Following addition of Protein A/G, reaction mixtures were held at room temperature while gently shaking for 1 hr to make bi-specific antibodies. Doxorubicin loaded minicells were washed twice by pelleting and resuspension in 980 µL of 1×PBS and 20 µL of bi-specific antibody complex added and co-incubated for 1 hr at 4° C. while gently shaking. Following attachment of antibodies to minicells, doxorubicin loaded antibody-coated minicells were washed twice by pelleting and resuspended in 12% D-trehalose to a concentration of $3.33 \times 10^{10}$/mL. Once formulated at the target concentration, doxorubicin-loaded, EGFR-1 targeted minicells were aseptically hand-filled by a semi-automated process into 5 mL amber serum vials, stoppered, over-sealed and frozen. Vials of doxorubicin-loaded EGFR-1 targeted minicells were gamma irradiated at a dose of 25 kGy while frozen and subject to analysis in comparison to non-irradiated controls. The presence of the anti-EGFR-1 antibodies and the retention of doxorubicin were verified by dual color flow cytometry using the natural red fluorescence of doxorubicin (upper left quadrant of control setup) and an Alexa-Flour 388-conjugated goat polyclonal anti-mouse antibody to detect mAb528 (lower right quadrant of control setup). Dual signal (upper right quadrant) indicates signal coming from minicells containing both doxorubicin and mAb528 on the minicell surface (i.e. double positive). After establishing control settings, preservation of mAb528 on the minicell surface and the retention of doxorubicin following gamma irradiation at 25 kGy was analyzed using this method. Doxorubicin retention was also monitored by fluorescence microscopy and macroscopic observation of minicell pellets before and after gamma irradiation at 25 kGy. The potency of EGFR-1 targeted, doxorubicin-loaded minicells was evaluated before and after gamma irradiation by titration against A549 human non-small cell carcinoma cells (overexpressing EGFR-1). As shown in FIGS. 7A-F, no differences in potency as determined by $EC_{50}$ curves were observed in response to increasing levels of gamma irradiation.

Figure 8A:
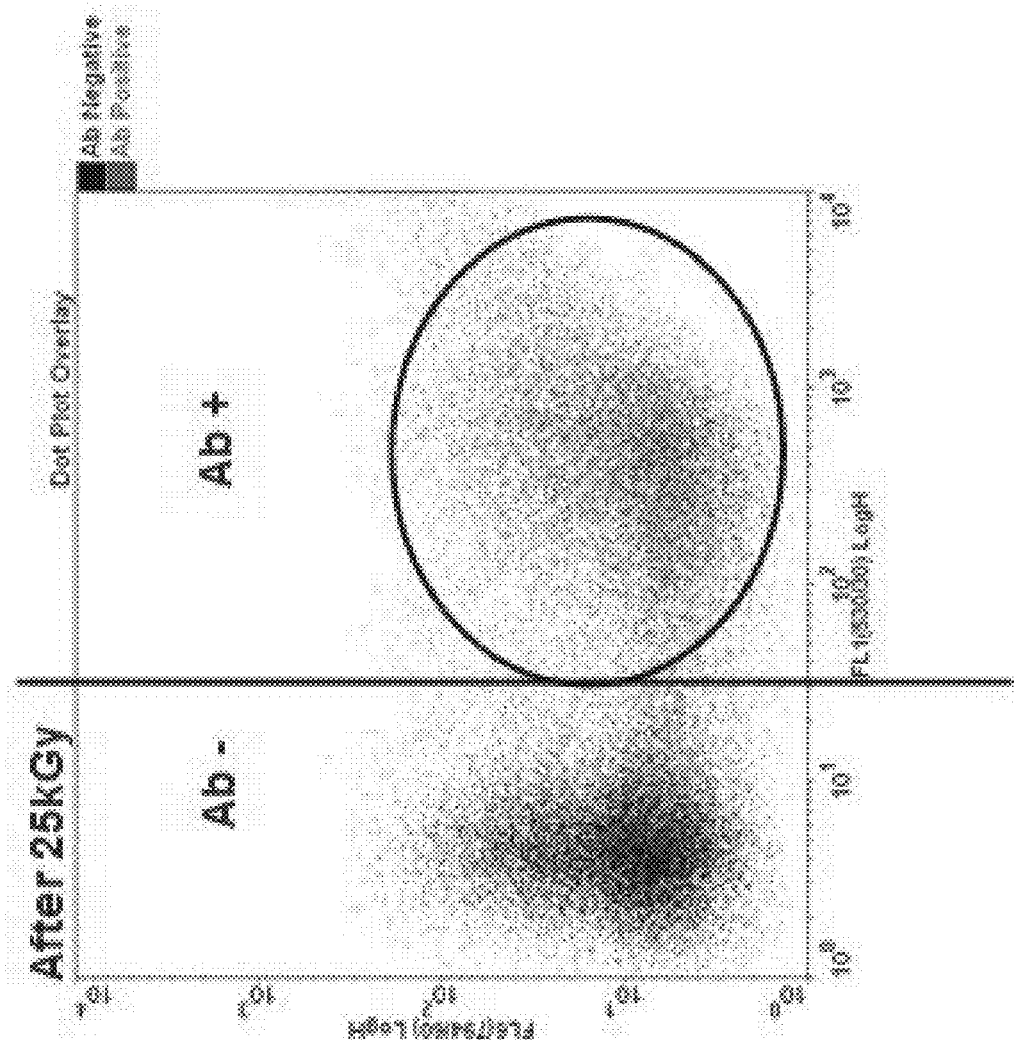
FIGS. 8A-B show no loss of stability or integrity of minicells after gamma irradiation at 25 kGy, where the minicells comprise a recombinant expression plasmid and display an antibody against human Epidermal Growth Factor Receptor 1 (EGFR-1) on their surfaces.
Figure 8B:
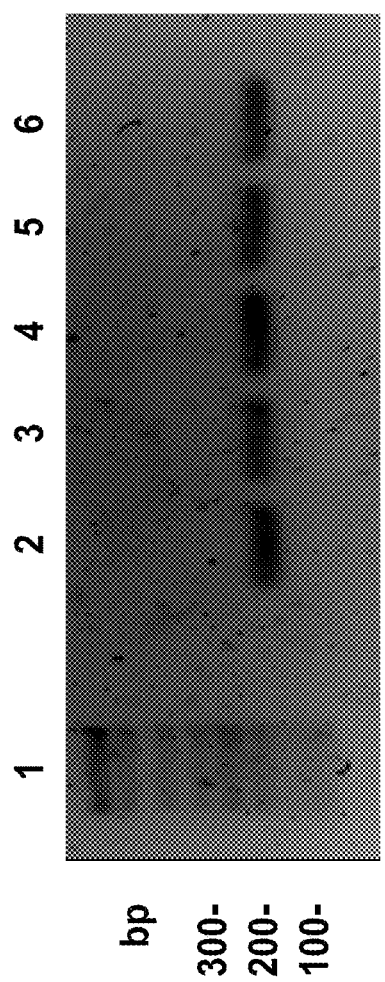

Stability of EGFR-1 targeted minicells comprising a functional nucleic acid (plasmid DNA) following gamma irradiation of frozen suspensions was studied. Plasmid integrity was evaluated using PCR with primers specific for the plasmid construct in minicells and in comparison to a naked plasmid control (plasmid control purified directly from equivalent number of minicells). The anti-EGFR-1 antibody, mAb528 was coupled to the surface of minicells using the same Protein A/G approach described above respect to FIGS. 7A-F and analyzed post irradiation for its presence on the minicell surface using the same flow cytometry approach and secondary Alexa Flour 388-conjugated goat anti-mouse polyclonal antibody reagent. As shown in FIGS. 8A-B, no loss in plasmid integrity or stability was observed after the minicell-containing frozen suspensions were exposed to gamma irradation.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein, including patents, patent applications, papers, text books, and the like, and the references cited herein, to the extent that they are not already, are hereby incorporated by reference in their entirety. In the event that one or more of the incorporated literature and similar materials differ from or contradict this application, including but not limited to defined terms, term usage, described techniques, or the like, this application controls.

What is claimed is:

1. A method of producing a terminally sterilized composition of bacterial minicells for pharmaceutical use, comprising exposing a composition comprising a plurality of bacterial minicells to gamma irradiation.

2. The method of claim 1, wherein said gamma irradiation is at a dose of about 5 kGy to about 40 kGy.

3. The method of claim 1, wherein the dose of the gamma irradiation is sufficient to sterilize the composition to a level conforming to USP <71> standards under version USP 38 NF 33.

4. The method of claim 1, wherein the composition is a pharmaceutical composition comprising a pharmaceutically acceptable excipient, a pharmaceutically acceptable diluent, or both.

5. The method of claim 4, wherein said pharmaceutically acceptable excipient is trehalose.

6. The method of claim 4, wherein said pharmaceutically acceptable diluent is sterile water for injection.

7. The method of claim 1, wherein said composition is in the form of a frozen suspension.

8. The method of claim 1, wherein said bacterial minicells display invasin, comprise perfringolysin O (PFO), or both.

9. The method of claim 1, wherein said composition is in the form of a frozen lyophile.

10. The method of claim 1, wherein said gamma irradiation is at a dose of about 25 kGy.

11. The method of claim 4, wherein said pharmaceutically acceptable diluent is sterile water.

12. The method of claim 8, wherein said invasin is an invasin from *Yersinia pseudotuberculosis*.

\* \* \* \* \*